(12) United States Patent
Mann et al.

(10) Patent No.: US 8,394,833 B2
(45) Date of Patent: Mar. 12, 2013

(54) METHODS OF TREATING EMESIS USING GROWTH HORMONE SECRETAGOGUES

(75) Inventors: William R. Mann, Sparta, NJ (US); William J. Polvino, Tinton Falls, NJ (US)

(73) Assignee: Helsinn Therapeutics (U.S.), Inc., Bridgewater, NJ (US)

( * ) Notice: Subject to any disclaimer, the term of this patent is extended or adjusted under 35 U.S.C. 154(b) by 0 days.

(21) Appl. No.: 13/476,111

(22) Filed: May 21, 2012

(65) Prior Publication Data

US 2012/0232113 A1 Sep. 13, 2012

Related U.S. Application Data

(62) Division of application No. 12/082,411, filed on Apr. 10, 2008.

(60) Provisional application No. 60/922,742, filed on Apr. 10, 2007.

(51) Int. Cl.
*A61K 31/454* (2006.01)
(52) U.S. Cl. ...................................... 514/323
(58) Field of Classification Search ................. None
See application file for complete search history.

(56) References Cited

U.S. PATENT DOCUMENTS

2008/0194672 A1* 8/2008 Hoveyda et al. ............... 514/450

* cited by examiner

*Primary Examiner* — Phyllis G. Spivack
(74) *Attorney, Agent, or Firm* — Arnall Golden Gregory LLP; Clark G. Sullivan

(57) ABSTRACT

The present invention relates to methods of treating emesis by administering to the subject an effective amount of a growth hormone secretagogue compound or a pharmaceutically acceptable salt thereof.

16 Claims, No Drawings

METHODS OF TREATING EMESIS USING GROWTH HORMONE SECRETAGOGUES

RELATED APPLICATIONS

This application claims the benefit of U.S. Provisional Application No. 60/922,742 filed Apr. 10, 2007. The entire contents of the aforementioned application are expressly incorporated herein by reference.

BACKGROUND OF THE INVENTION

Emesis is a well-known and frequent side-effect of cancer chemotherapeutic agents, such as cisplatin. It causes serious problems in cancer chemotherapy, and in some patients emesis is so severe that therapy must be discontinued. Anti-emetic agents are therefore often administered in order to alleviate this side-effect of the cancer chemotherapeutic agent. The anti-emetic agents employed are usually benzamide derivatives, such as metoclopramide, which have dopamine antagonist activity. In view of their dopamine antagonist activity benzamide derivatives such as metoclopramide themselves exhibit serious and undesirable side-effects, such as extra-pyramidal effects, i.e. tardive dyskinesia, acute dystonia, akathisia and tremor. Other anti-emetic drugs include 5-HT3 antagonists, e.g., ondansetron; corticosteroids, e.g., dexamethasone; and NK1 antagonists, e.g., aprepitant. These treatments fail to adequately address the needs of the patient.

In view of the above, an effective treatment for emesis that minimizes or eliminates one or more of the side effects of therapies that are currently available is highly desirable.

SUMMARY OF THE INVENTION

The present invention relates to methods and compositions for treating subjects having or at risk of having emesis. The invention also provides methods and compositions for the treatment of cancer symptom burden as measured by the ASAS test. The methods comprise administering to a subject in need thereof a therapeutically effective amount of a growth hormone secretagogue compound or a pharmaceutically acceptable salt, hydrate or solvate thereof.

The compositions and methods of the invention are useful for providing relief to a patient experiencing an emetogenic condition or those experiencing symptoms of cancer. The present composition is particularly efficacious for treating patients undergoing, about to undergo, or recovering from chemotherapy for a deadly disease, such as cancer. However, other conditions, such as vertigo, motion sickness, AIDS, food poisoning and other acute or chronic diseases and infections that cause nausea, emesis, or associated symptoms thereof, may be effectively treated by the compositions and methods disclosed herein.

Specifically, the invention provides a method for treating emesis in a subject in need thereof, by administering to the subject an effective amount of a growth hormone secretagogue. Exemplary growth hormone secretagogues are represented by Formulas I-V, or a pharmaceutically acceptable salt, hydrate, amides or solvate thereof.

One growth hormone secretagogue is represented by the structural Formula I:

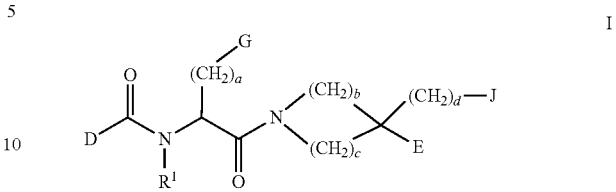

wherein:

$R^1$ is hydrogen, or $C_{1-6}$-alkyl optionally substituted with one or more aryl or hetaryl;

a and d are independently 0, 1, 2 or 3;

b and c are independently 0, 1, 2, 3, 4 or 5, provided that b+c is 3, 4 or 5;

D is $R^2$—NH—$(CR^3R^4)_e$—$(CH_2)_f$-M-$(CHR^5)_g$—$(CH_2)_h$— wherein:

$R^2$, $R^3$, $R^4$ and $R^5$ are independently hydrogen or $C_{1-6}$ alkyl optionally substituted with one or more halogen, amino, hydroxyl, aryl or hetaryl; or $R^2$ and $R^3$ or $R^2$ and $R^4$ or $R^3$ and $R^4$ can optionally form —$(CH_2)_i$—U—$(CH_2)_j$—, wherein i and j are independently 1 or 2 and U is —O—, —S— or a valence bond;

h and f are independently 0, 1, 2, or 3;

g and e are independently 0 or 1;

M is a valence bond, —$CR^6$=$CR^7$—, arylene, hetarylene, —O— or —S—;

$R^6$ and $R^7$ are independently hydrogen, or $C_{1-6}$-alkyl optionally substituted with one or more aryl or hetaryl;

G is —O—$(CH_2)_k$—$R^8$,

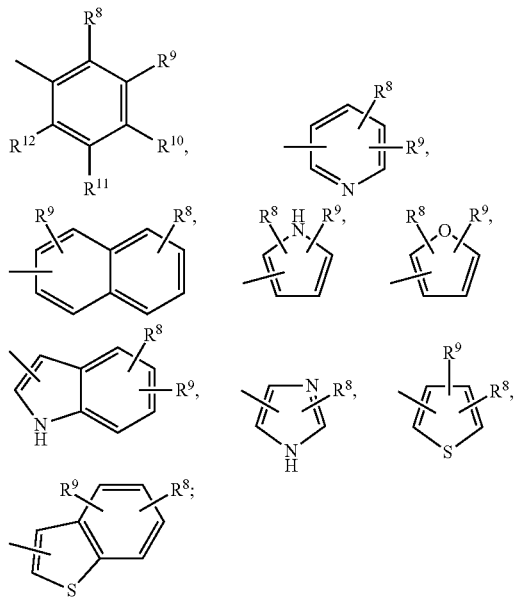

J is —O—$(CH_2)_l$—$R^{13}$,

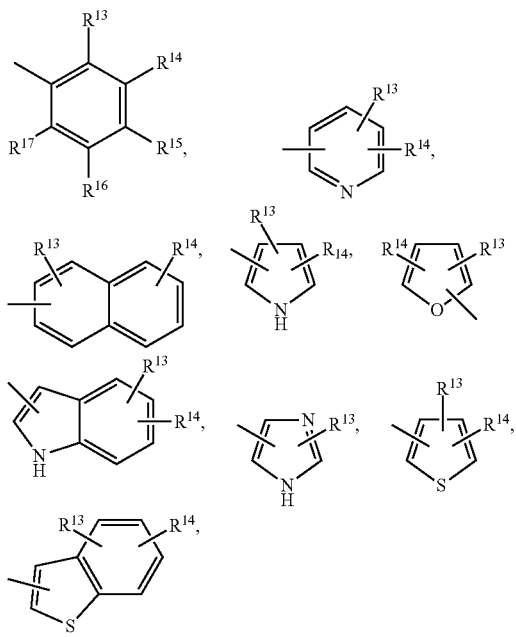

wherein:

R$^8$, R$^9$, R$^{10}$, R$^{11}$, R$^{12}$, R$^{13}$, R$^{14}$, R$^{15}$, R$^{16}$ and R$^{17}$ independently are hydrogen, halogen, aryl, hetaryl, C$_{1-6}$-alkyl or C$_{1-6}$-alkoxy;

k and l are independently 0, 1 or 2;

E is —CONR$^{18}$R$^{19}$, —COOR$^{19}$, —(CH$_2$)$_m$—NR$^{18}$SO$_2$R$^{20}$, —(CH$_2$)$_m$—NR$^{18}$—COR$^{20}$, —(CH$_2$)$_m$—OR$^{19}$, —(CH$_2$)$_m$—OCOR$^{20}$, —CH(R$^{18}$)R$^{19}$, —(CH$_2$)$_m$—NR$^{18}$—CS—NR$^{19}$R$^{21}$ or —(CH$_2$)$_m$—NR$^{18}$—CO—NR$^{19}$R$^{21}$; or

E is —CONR$^{22}$NR$^{23}$R$^{24}$, wherein R$^{22}$ is hydrogen, C$_{1-6}$-alkyl optionally substituted with one or more aryl or hetaryl, or aryl or hetaryl optionally substituted with one or more C$_{1-6}$-alkyl; R$^{23}$ is C$_{1-6}$-alkyl optionally substituted with one or more aryl or hetaryl, or C$_{1-7}$-acyl; and R$^{24}$ is hydrogen, C$_{1-6}$-alkyl optionally substituted with one or more aryl or hetaryl; or aryl or hetaryl optionally substituted with one or more C$_{1-6}$-alkyl; or R$^{22}$ and R$^{23}$ together with the nitrogen atoms to which they are attached can form a heterocyclic system optionally substituted with one or more C$_{1-6}$-alkyl, halogen, amino, hydroxyl, aryl or hetaryl; or R$^{22}$ and R$^{24}$ together with the nitrogen atoms to which they are attached can form a heterocyclic system optionally substituted with one or more C$_{1-6}$-alkyl, halogen, amino, hydroxyl, aryl or hetaryl; or R$^{23}$ and R$^{24}$ together with the nitrogen atom to which they are attached can form a heterocyclic system optionally substituted with one or more C$_{1-6}$-alkyl, halogen, amino, hydroxyl, aryl or hetaryl;

wherein m is 0, 1, 2 or 3,

R$^{18}$, R$^{19}$ and R$^{21}$ independently are hydrogen or C$_{1-6}$-alkyl optionally substituted with halogen, —N(R$^{25}$)R$^{26}$, wherein R$^{25}$ and R$^{26}$ are independently hydrogen or C$_{1-6}$ alkyl; hydroxyl, C$_{1-6}$-alkoxy, C$_{1-6}$-alkoxycarbonyl, C$_{1-6}$-alkylcarbonyloxy or aryl;

or R$^{19}$ is

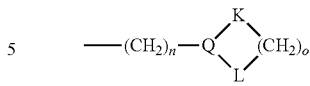

wherein
Q is —CH< or —N<,
K and L are independently —CH$_2$—, —CO—, —O—, —S—, —NR$^{27}$— or a valence bond, where R$^{27}$ is hydrogen or C$_{1-6}$ alkyl;
n and o are independently 0, 1, 2, 3 or 4;
R$^{20}$ is C$_{1-6}$ alkyl, aryl or hetaryl;
or a pharmaceutically acceptable salt thereof;
with the proviso that if M is a valence bond then E is —CONR$^{22}$NR$^{23}$R$^{24}$.

The compounds of Formula I are fully described in U.S. Pat. No. 6,303,620 to Hansen, et al., the entire content of which is hereby incorporated by reference.

One growth hormone secretagogue of Formula I is more specifically represented by the structural Formula II:

II

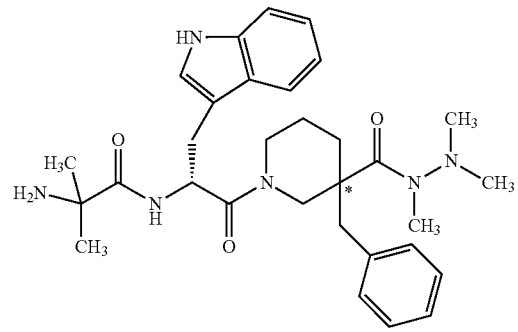

or a pharmaceutically acceptable salt, solvate or hydrate thereof.

The compounds of Formula II are fully described in U.S. Pat. No. 6,303,620 to Hansen, et al., the entire content of which is hereby incorporated by reference.

Another growth hormone secretagogue is represented by the structural Formula III:

III

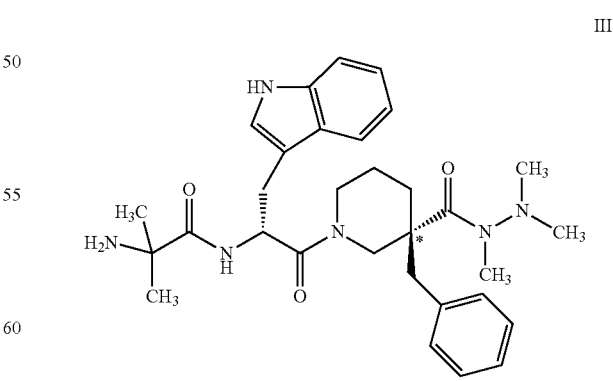

or a pharmaceutically acceptable salt, solvate or hydrate thereof.

The compound of Formula III is fully described in U.S. Pat. No. 6,576,648 to Hansen, et al., the entire content of which is hereby incorporated by reference. The chemical name of the compound of Formula III is 2-Amino-N-{(1R)-2-[3-benzyl-3-(N,N',N'-trimethylhydrazinocarbonyl)piperidin-1-yl]-1-((1H-indol-3-yl)-2-oxoethyl}-2-methylpropionamide, and is referred to as RC-1291 and anamorelin.

Another growth hormone secretagogue is represented by the structural Formula IV:

IV

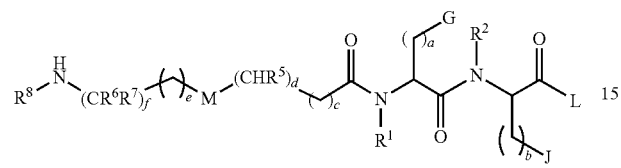

wherein $R^1$ is hydrogen or $C_{1-6}$-alkyl;

$R^2$ is hydrogen or $C_{1-6}$-alkyl;

L is

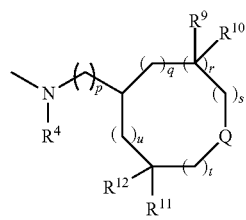

wherein $R^4$ is hydrogen or $C_{1-6}$ alkyl;

p is 0 or 1;

q, s, t, u are independently 0, 1, 2, 3, or 4;

r is 1;

the sum q+r+s+t+u is 0, 1, 2, 3, or 4;

$R^9$, $R^{10}$, $R^{11}$, and $R^{12}$ are independently hydrogen or $C_{1-6}$ alkyl;

Q is >N—$R^{13}$ or

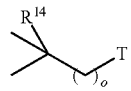

wherein:

o is 0, 1 or 2;

T is —N($R^{15}$)($R^{16}$) or hydroxyl;

$R^{13}$, $R^{15}$, and $R^{16}$ are independently hydrogen or $C_{1-6}$ alkyl;

$R^{14}$ is hydrogen, aryl or hetaryl;

Or L is

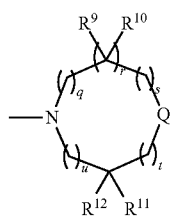

wherein p is 0 or 1;

q, s, t, u are independently 0, 1, 2, 3, or 4;

r is 0 or 1;

the sum q+r+s+t+u is 0, 1, 2, 3, or 4;

$R^9$, $R^{10}$, $R^{11}$, and $R^{12}$ are independently hydrogen or $C_{1-6}$ alkyl;

Q is >N—$R^{13}$ or

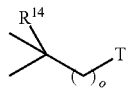

wherein o is 0, 1, or 2;

T is —N($R^{15}$)($R^{16}$) or hydroxyl;

$R^{13}$, $R^{15}$, and $R^{16}$ are independently from each other hydrogen or $C_{1-6}$ alkyl;

$R^{14}$ is hydrogen, aryl, or hetaryl;

G is —O—(CH$_2$)—$R^{17}$,

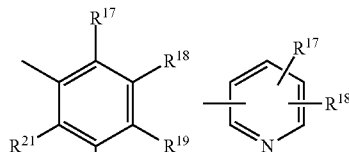

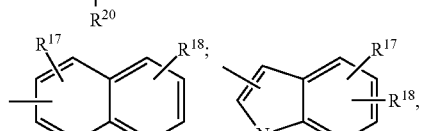

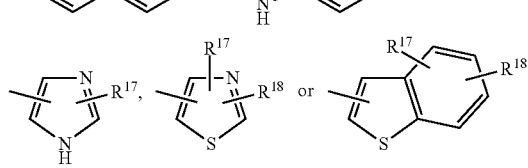

wherein:

$R^{17}$, $R^{18}$, $R^{19}$, $R^{20}$ and $R^{21}$ independently are hydrogen, halogen, aryl, hetaryl, $C_{1-6}$-alkyl or $C_{1-6}$-alkoxy;

K is 0, 1 or 2;

J is —O—(CH$_2$)$_l$—$R^{22}$,

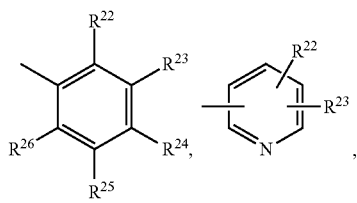

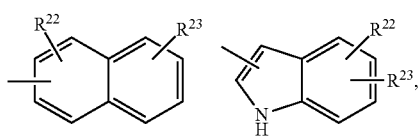

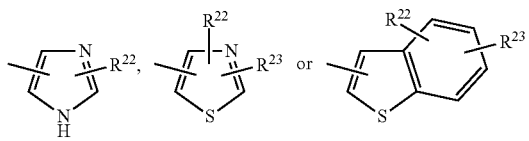

wherein:

$R^{22}$, $R^{23}$, $R^{24}$, $R^{25}$ and $R^{26}$ independently are hydrogen, halogen, aryl, hetaryl, $C_{1-6}$-alkyl or $C_{1-6}$-alkoxy;

l is 0, 1 or 2;

a is 0, 1, or 2;

b is 0, 1, or 2;

c is 0, 1, or 2;

d is 0 or 1;

e is 0, 1, 2, or 3;

f is 0 or 1;

$R^5$ is hydrogen or $C_{1-6}$-alkyl optionally substituted with one or more hydroxyl, aryl or hetaryl;

$R^6$ and $R^7$ are independently hydrogen or $C_{1-6}$-alkyl, optionally substituted with one or more halogen, amino, hydroxyl, aryl, or hetaryl;

$R^8$ is hydrogen or $C_{1-6}$-alkyl, optionally substituted with one or more halogen, amino, hydroxyl, aryl, or hetaryl;

$R^6$ and $R^7$ or $R^6$ and $R^8$ or $R^7$ and $R^8$ can optionally form —$(CH_2)_i$—U—$(CH_2)_j$—, wherein i and j independently are 1, 2 or 3 and U is —O—, —S—, or a valence bond;

M is arylene, hetarylene, —O—, —S— or —$CR^{27}$=$CR^{28}$—;

$R^{27}$ and $R^{28}$ are independently hydrogen or $C_{1-6}$-alkyl, optionally substituted with one or more aryl or hetaryl;

or a pharmaceutically acceptable salt thereof.

The compounds of Formula IV are fully described in U.S. Pat. No. 6,919,315 to Peschke, et al., the entire content of which is hereby incorporated by reference.

Another growth hormone secretagogue of Formula IV is more specifically represented by the structural Formula VI:

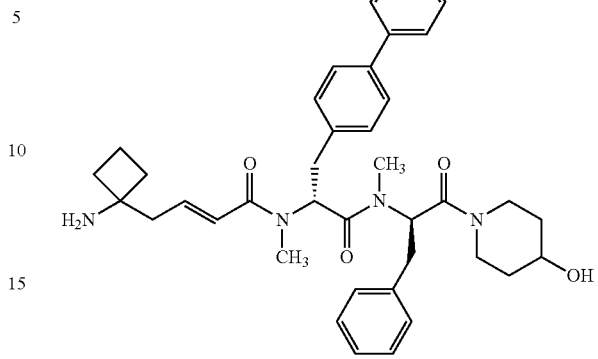

or a pharmaceutically acceptable salt, solvate or hydrate thereof.

The chemical name of the compound of Formula VI is: (2E)-4-(1-aminocyclobutyl)but-2-enoic acid N-((1R)-1-{N-[(1R)-1-benzyl-2-(4-hydroxypiperidin-1-yl)-2-oxoethyl]-N-methylcarbomoyl}-2-(biphenyl-4-yl)ethyl)-N-methylamide.

The compound of Formula VI is fully described in U.S. Pat. No. 6,919,315 to Peschke, et al., the entire content of which is hereby incorporated by reference.

The invention further provides kits and pharmaceutical compositions comprising the growth hormone secretagogues of the invention for the treatment of emesis, nausea or vomiting. The kits and pharmaceutical compositions may further comprise one or more additional anti-emetogenic, anti-nausea or anti-nausea compositions. Preferred pharmaceutical compositions of the invention comprise the compound of Formula III formulated to be administered orally for the treatment of emesis.

DETAILED DESCRIPTION OF THE INVENTION

The present invention is based on the unexpected finding that orally administered ghrelin receptor agonists reduced nausea when administered to cancer patients and reduces the cancer symptom burden of subject having cancer and/or undergoing cancer treatment. Accordingly, the present invention provides methods and compositions for the treatment or prevention of nausea and emetic syndromes and for reducing a subject's cancer symptom burden. The methods comprise administering to a subject in need thereof a therapeutically effective amount of a growth hormone secretagogue compound or a pharmaceutically acceptable salt, hydrate or solvate thereof. The growth hormone secretagogue is a compound represented by any of Formulas I-XVI, or a pharmaceutically acceptable salt, hydrate, amine or solvate thereof.

The invention also provides methods of treating or preventing nausea or emetic conditions by administering a therapeutically effective amount of a growth hormone secretagogue compound or a pharmaceutically acceptable salt, hydrate or solvate thereof, further comprise administering one or more additional antiemetic agents. The methods and compositions of the invention are useful, for example, for treating or preventing nausea in subjects receiving chemotherapeutic treatment for a cell proliferative disorder, e.g., cancer.

Growth Hormone Secretagogues/Ghrelin Agonists

As used herein, "growth hormone secretagogue" refers to a substance (e.g., a molecule, a compound) which promotes (induces or enhances) at least one function characteristic of a growth hormone secretagogue receptor (GHS receptor). Exemplary growth hormones secretagogues are ghrelins mimetics such as ghrelin agonists. In one embodiment, the growth hormone secretagogue compound or ghrelin agonist binds the GHS receptor or ghrelin receptor (i.e., is a ghrelin or GHS receptor agonist) and induces the secretion of growth hormone. A compound having GHS receptor agonist activity (e.g., a GHS receptor or ghrelin receptor agonist) can be identified and activity assessed by any suitable method. For example, the binding affinity of a GHS receptor agonist to the GHS receptor can be determined employing receptor binding assays and growth hormone stimulation can be assessed as described in U.S. Pat. No. 6,919,315, incorporated herein by reference.

GHS or ghrelin (GRLN) receptors are expressed in the hypothalamus, pituitary and pancreas, among other tissues. Activation of these receptors in the pituitary induces the secretion of growth hormone. In addition to inducing the secretion of growth hormone, recent studies have shown the growth hormone secretagogues can increase appetite and body weight. At typical doses, growth hormone secretagogues are also known to induce the secretion of IGF-1. Exemplary growth hormone secretagogue compounds are those described in U.S. Pat. Nos. 6,303,620, 6,576,648, 5,977,178, 6,566,337, 6,083,908, 6,274,584 and U.S. Pat. No. 6,919,315, the entire content of all of which are incorporated herein by reference.

Another the growth hormone secretagogue is represented by the structural Formula I:

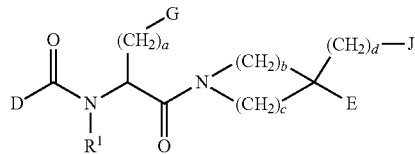

I wherein:
$R^1$ is hydrogen, or $C_{1-6}$-alkyl optionally substituted with one or more aryl or hetaryl;
a and d are independently 0, 1, 2 or 3;
b and c are independently 0, 1, 2, 3, 4 or 5, provided that b+c is 3, 4 or 5;
D is $R^2$—NH—$(CR^3R^4)_e$—$(CH_2)_f$-M-$(CHR^5)_g$—$(CH_2)_h$—
wherein:
$R^2$, $R^3$, $R^4$ and $R^5$ are independently hydrogen or $C_{1-6}$ alkyl optionally substituted with one or more halogen, amino, hydroxyl, aryl or hetaryl; or
$R^2$ and $R^3$ or $R^2$ and $R^4$ or $R^3$ and $R^4$ can optionally form —$(CH_2)_i$—U—$(CH_2)_j$—, wherein i and j are independently 1 or 2 and U is —O—, —S— or a valence bond;
h and f are independently 0, 1, 2, or 3;
g and e are independently 0 or 1;
M is a valence bond, —$CR^6$=$CR^7$—, arylene, hetarylene, —O— or —S—;
$R^6$ and $R^7$ are independently hydrogen, or $C_{1-6}$-alkyl optionally substituted with one or more aryl or hetaryl;
G is —O—$(CH_2)_k$—$R^8$,

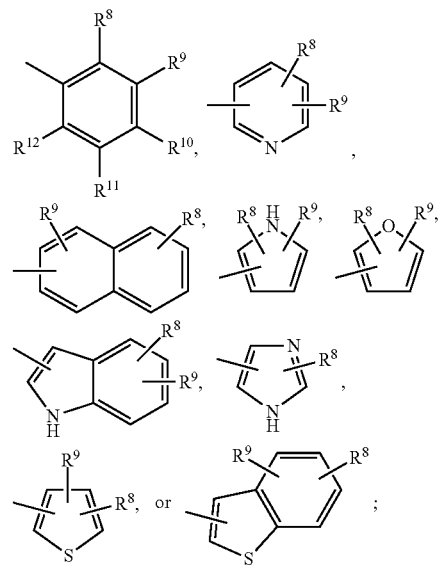

J is —O—$(CH_2)_l$—$R^{13}$,

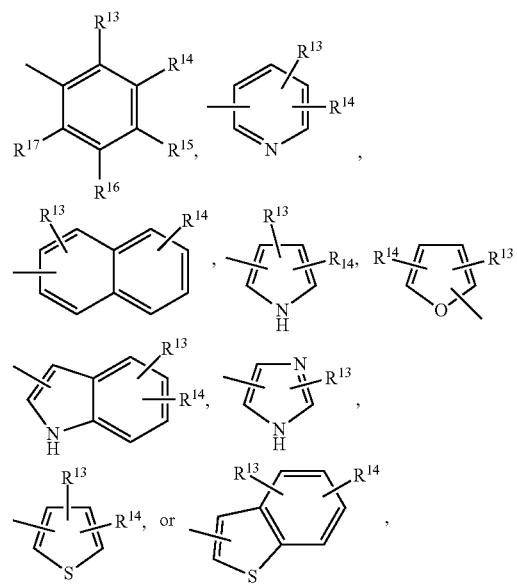

wherein:
$R^8$, $R^9$, $R^{10}$, $R^{11}$, $R^{12}$, $R^{13}$, $R^{14}$, $R^{15}$, $R^{16}$ and $R^{17}$ independently are hydrogen, halogen, aryl, hetaryl, $C_{1-6}$-alkyl or $C_{1-6}$-alkoxy;
k and l are independently 0, 1 or 2;
E is —$CONR^{18}R^{19}$, —$COOR^{19}$, —$(CH_2)_m$—$NR^{18}SO_2R^{20}$, —$(CH_2)_m$—$NR^{18}$—$COR^{20}$, —$(CH_2)_m$—$OR^{19}$, —$(CH_2)_m$—$OCOR^{20}$, —$CH(R^{18})R^{19}$, —$(CH_2)_m$—$NR^{18}$—$CS$—$NR^{19}R^{21}$ or —$(CH_2)_m$—$NR^{18}$—$CO$—$NR^{19}R^{21}$; or
E is —$CONR^{22}NR^{23}R^{24}$, wherein $R^{22}$ is hydrogen, $C_{1-6}$-alkyl optionally substituted with one or more aryl or hetaryl, or aryl or hetaryl optionally substituted with one or more $C_{1-6}$-alkyl; $R^{23}$ is $C_{1-6}$-alkyl optionally substituted with one or more aryl or hetaryl, or $C_{1-7}$-acyl; and $R^{24}$ is hydrogen, $C_{1-6}$-alkyl optionally substituted with one or more aryl or hetaryl; or aryl or hetaryl optionally substituted with one or more $C_{1-6}$-alkyl; or R²² and R²³ together with the nitrogen atoms to which they are attached can form a heterocyclic system optionally substituted with one or more $C_{1-6}$-alkyl, halogen, amino, hydroxyl, aryl or hetaryl; or R²² and R²⁴ together with the nitrogen atoms to which they are attached can form a heterocyclic system optionally substituted with one or more $C_{1-6}$-alkyl, halogen, amino, hydroxyl, aryl or hetaryl; or R²³ and R²⁴ together with the nitrogen atom to which they are attached can form a heterocyclic system optionally substituted with one or more $C_{1-6}$-alkyl, halogen, amino, hydroxyl, aryl or hetaryl;

wherein m is 0, 1, 2 or 3, $R^{18}$, $R^{19}$ and $R^{21}$ independently are hydrogen or $C_{1-6}$-alkyl optionally substituted with halogen, —N(R²⁵)R²⁶, wherein $R^{25}$ and $R^{26}$ are independently hydrogen or $C_{1-6}$ alkyl; hydroxyl, $C_{1-6}$-alkoxy, $C_{1-6}$-alkoxycarbonyl, $C_{1-6}$-alkylcarbonyloxy or aryl;

or $R^{19}$ is

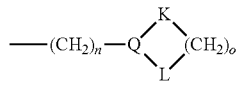

wherein

Q is —CH< or —N<,

K and L are independently —CH₂—, —CO—, —O—, —S—, —NR²⁷— or a valence bond, where $R^{27}$ is hydrogen or $C_{1-6}$ alkyl;

n and o are independently 0, 1, 2, 3 or 4;

$R^{20}$ is $C_{1-6}$ alkyl, aryl or hetaryl;

or a pharmaceutically acceptable salt thereof;

with the proviso that if M is a valence bond then E is —CONR²²NR²³R²⁴.

$R^1$ may be $C_{1-6}$-alkyl. a may be 1.

d may be 1, or, b+c is 4.

D is

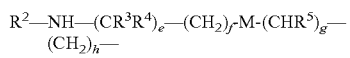

wherein $R^2$, $R^3$, $R^4$ and $R^5$ are independently hydrogen or $C_{1-6}$ alkyl optionally substituted with a halogen, amino, hydroxyl, aryl or hetaryl; or $R^2$ and $R^3$ or $R^2$ and $R^4$ or $R^3$ and $R^4$ can optionally form —(CH₂)ᵢ—U—(CH₂)ⱼ—, wherein i and j are independently 1 or 2 and U is —O—, —S— or a valence bond;

h and f are independently 0, 1, 2, or 3;

g and e are independently 0 or 1;

M is —CR⁶=CR⁷—, arylene, hetarylene, —O— or —S—; and $R^6$ and $R^7$ are independently hydrogen, or $C_{1-6}$-alkyl.

In a further embodiment, D is

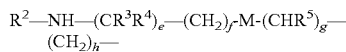

wherein:

$R^2$, $R^3$, $R^4$ and $R^5$ are independently hydrogen or $C_{1-6}$ alkyl optionally substituted with a halogen, amino, hydroxyl, aryl or hetaryl; or $R^2$ and $R^3$ or $R^2$ and $R^4$ or $R^3$ and $R^4$ can optionally form —(CH₂)ᵢ—U—(CH₂)ⱼ—, wherein i and j are independently 1 or 2 and U is —O—, —S— or a valence bond;

h and f are independently 0, 1, 2, or 3; g and e are independently 0 or 1; M is a valence bond.

G may be

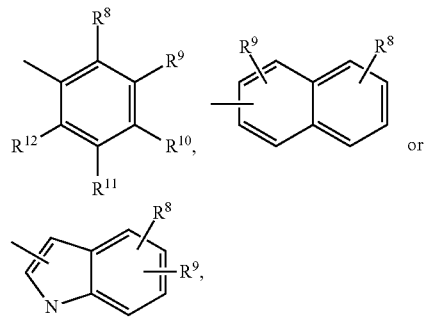

wherein:

$R^8$, $R^9$, $R^{10}$, $R^{11}$ and $R^{12}$ independently are hydrogen, halogen, aryl, hetaryl, $C_{1-6}$-alkyl or $C_{1-6}$ alkoxy; and k is 0, or 2.

J may be

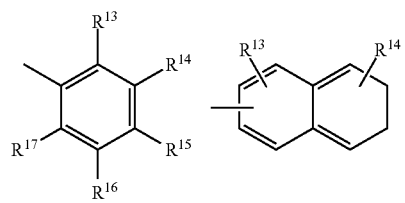

wherein:

$R^{13}$, $R^{14}$, $R^{15}$, $R^{16}$ and $R^{17}$ independently are hydrogen, halogen, aryl, hetaryl, $C_{1-6}$-alkyl or $C_{1-6}$-alkoxy.

E may be —CONR¹⁸R¹⁹, —COOR¹⁹ or —(CH₂)ₘ—OR¹⁹, wherein:

m is 0, 1, 2 or 3;

$R^{18}$ and $R^{19}$ independently are hydrogen or $C_{1-6}$-alkyl optionally substituted by halogen, —N(R²⁵)R²⁶ wherein $R^{25}$ and $R^{26}$ are independently hydrogen or $C_{1-6}$ alkyl; hydroxyl, $C_{1-6}$-alkoxy, $C_{1-6}$-alkoxycarbonyl, $C_{1-6}$-alkylcarbonyloxy or aryl.

E may also be —CONR²²NR²³R²⁴ wherein:

$R^{22}$ is hydrogen, $C_{1-6}$-alkyl optionally substituted with an aryl or hetaryl, or aryl or hetaryl optionally substituted with a $C_{1-6}$-alkyl;

$R^{23}$ is $C_{1-6}$-alkyl optionally substituted with one or more aryl or hetaryl, or $C_{1-7}$-acyl; and $R^{24}$ is hydrogen, $C_{1-6}$-alkyl optionally substituted with an aryl or hetaryl; or aryl or hetaryl optionally substituted with a $C_{1-6}$-alkyl; or R²² and R²³ together with the nitrogen atoms to which they are attached can form a heterocyclic system optionally substituted with a $C_{1-6}$-alkyl, halogen, amino, hydroxyl, aryl or hetaryl; or R²² and R²⁴ together with the nitrogen atoms to which they are attached can form a heterocyclic system optionally substituted with a $C_{1-6}$-alkyl, halogen, amino, hydroxyl, aryl or hetaryl; or R²³ and R²⁴ together with the nitrogen atom to which they are attached can form a heterocyclic system optionally substituted with a $C_{1-6}$-alkyl, halogen, amino, hydroxyl, aryl or hetaryl.

Another growth hormone secretagogue is represented by the structural Formula II:

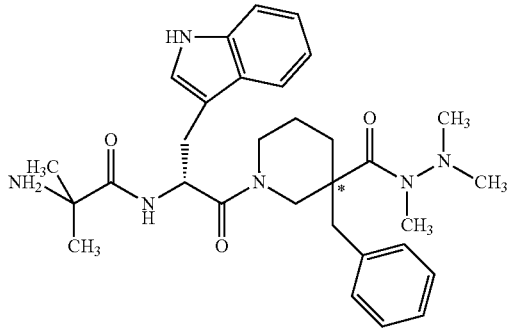

II

One exemplary compound of Formula II has the (R) configuration at the chiral carbon designated by the asterisk (*) in Formula II. The chemical name of the compound of Formula II having the (R) configuration at the designated chiral carbon is: 2-Amino-N-{(1R)-2-[3-benzyl-3-(N,N',N'-trimethylhydrazinocarbonyl)piperidin-1-yl]-1-((1H-indol-3-yl)-2-oxo-ethyl}-2-methylpropionamide, represented by structural Formula III:

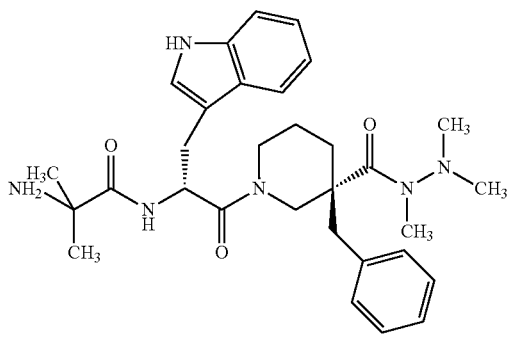

III and pharmaceutically acceptable salts thereof.

Another growth hormone secretagogue is represented by the structural Formula IV:

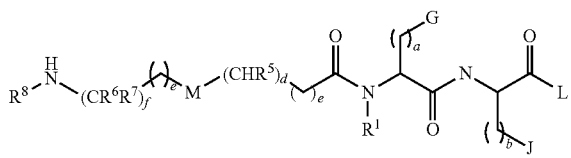

IV wherein
R$^1$ is hydrogen or C$_{1-6}$-alkyl;
R$^2$ is hydrogen or C$_{3-6}$-alkyl;

L is

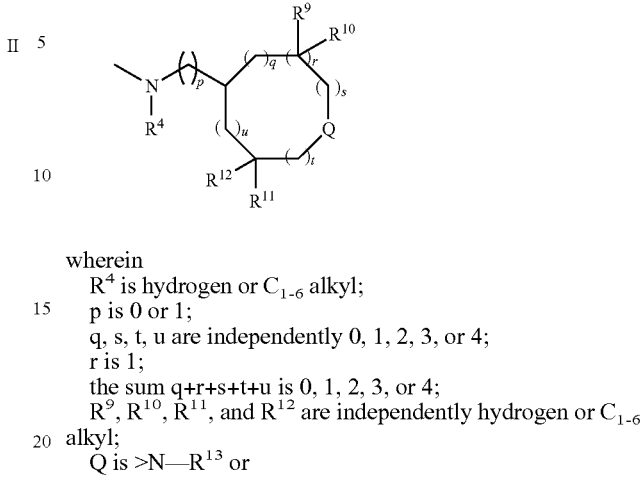

wherein
R$^4$ is hydrogen or C$_{1-6}$ alkyl;
p is 0 or 1;
q, s, t, u are independently 0, 1, 2, 3, or 4;
r is 1;
the sum q+r+s+t+u is 0, 1, 2, 3, or 4;
R$^9$, R$^{10}$, R$^{11}$, and R$^{12}$ are independently hydrogen or C$_{1-6}$ alkyl;
Q is >N—R$^{13}$ or

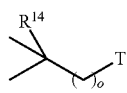

wherein:
o is 0, 1 or 2;
T is —N(R$^{15}$)(R$^{16}$) or hydroxyl;
R$^{13}$, R$^{15}$, and R$^{16}$ are independently hydrogen or C$_{1-6}$ alkyl;
R$^{14}$ is hydrogen, aryl or hetaryl;
Or L is

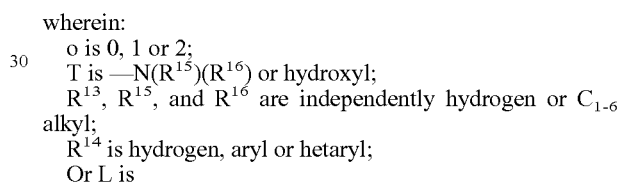

wherein
p is 0 or 1;
q, s, t, u are independently 0, 1, 2, 3, or 4;
r is 0 or 1;
the sum q+r+s+t+u is 0, 1, 2, 3, or 4;
R$^9$, R$^{10}$, R$^{11}$, and R$^{12}$ are independently hydrogen or C$_{1-6}$ alkyl;
Q is >N—R$^{13}$ or

wherein
o is 0, 1, or 2;
T is —N(R$^{15}$)(R$^{16}$) or hydroxyl;
R$^{13}$, R$^{15}$, and R$^{16}$ are independently from each other hydrogen or C$_{1-6}$ alkyl;
R$^{14}$ is hydrogen, aryl, or hetaryl;
G is —O—(CH$_2$)—R$^{17}$,

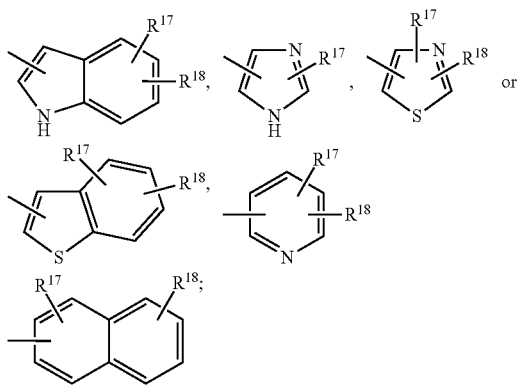

wherein:
$R^{17}$, $R^{18}$, $R^{19}$, $R^{20}$ and $R^{21}$ independently are hydrogen, halogen, aryl, hetaryl, $C_{1-6}$-alkyl or $C_{1-6}$-alkoxy;
K is 0, 1 or 2;
J is —O—$(CH_2)_l$—$R^{22}$,

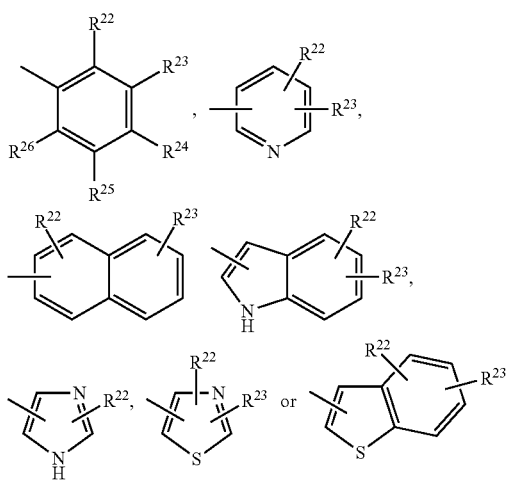

wherein:
$R^{22}$, $R^{23}$, $R^{24}$, $R^{25}$ and $R^{26}$ independently are hydrogen, halogen, aryl, hetaryl, $C_{1-6}$-alkyl or $C_{1-6}$-alkoxy;
l is 0, 1 or 2;
a is 0, 1, or 2;
b is 0, 1, or 2;
c is 0, 1, or 2;
d is 0 or 1;
e is 0, 1, 2, or 3;
f is 0 or 1;
$R^5$ is hydrogen or $C_{1-6}$-alkyl optionally substituted with one or more hydroxyl, aryl or hetaryl;
$R^6$ and $R^7$ are independently hydrogen or $C_{1-6}$-alkyl, optionally substituted with one or more halogen, amino, hydroxyl, aryl, or hetaryl;
$R^8$ is hydrogen or $C_{1-6}$-alkyl, optionally substituted with one or more halogen, amino, hydroxyl, aryl, or hetaryl;
$R^6$ and $R^7$ or $R^6$ and $R^8$ or $R^7$ and $R^8$ can optionally form —$(CH_2)_i$—U—$(CH_2)_j$—, wherein i and j independently are 1, 2 or 3 and U is —O—, —S—, or a valence bond;
M is arylene, hetarylene, —O—, —S— or —$CR^{27}$=$CR^{28}$—;
$R^{27}$ and $R^{28}$ are independently hydrogen or $C_{1-6}$-alkyl, optionally substituted with one or more aryl or hetaryl;
or a pharmaceutically acceptable salt thereof.
$R^1$ may be $C_{1-6}$-alkyl.
$R^2$ may be $C_{1-6}$-alkyl.
L may be

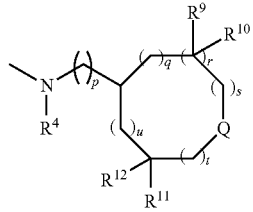

wherein $R^4$ is hydrogen or $C_{1-6}$ alkyl;
p is 0 or 1;
q, s, t, u are independently from each other 0, 1, 2, 3 or 4;
r is 0 or 1;
the sum q+r+s+t+u is 0, 1, 2, 3, or 4;
$R^9$, $R^{10}$, $R^{11}$, and $R^{12}$ are independently from each other hydrogen or $C_{1-6}$ alkyl;
Q is >N—$R^{13}$ or

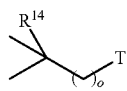

wherein:
o is 0, 1 or 2;
T is —N($R^{15}$)($R^{16}$) or hydroxyl;
$R^{13}$, $R^{15}$, and $R^{16}$ are independently from each other hydrogen or $C_{1-6}$ alkyl; and
$R^{14}$ is hydrogen, aryl or hetaryl.
L may be

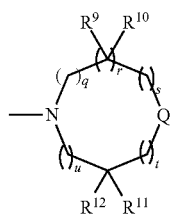

wherein:
q, s, t, u are independently from each other 0, 1, 2, 3 or 4;
r is 0 or 1;
the sum q+r+s+t+u is 0, 1, 2, 3, or 4;
$R^9$, $R^{10}$, $R^{11}$, and $R^{12}$ are independently from each other hydrogen or $C_{1-6}$ alkyl;
Q is >N—$R^{13}$ or

wherein:
o is 0, 1 or 2;
T is —N($R^{15}$)($R^{16}$) or hydroxyl;

$R^{13}$, $R^{15}$, and $R^{16}$ are independently from each other hydrogen or $C_{1-6}$ alkyl; and $R^{14}$ is hydrogen, aryl or hetaryl.

G may be

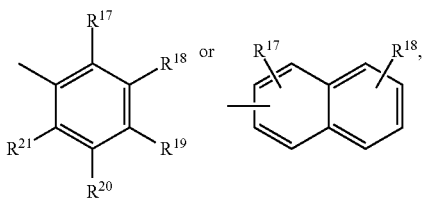

wherein:

$R^{17}$, $R^{18}$, $R^{19}$, $R^{20}$ and $R^{21}$ independently from each other are hydrogen, halogen, aryl, hetaryl, $C_{1-6}$-alkyl or $C_{1-6}$-alkoxy.

J may be

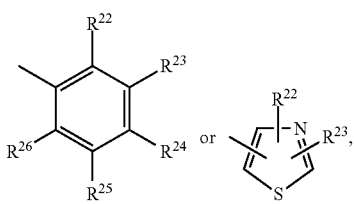

wherein:

$R^{22}$, $R^{23}$, $R^{24}$, $R^{25}$ and $R^{26}$ independently from each other are hydrogen, halogen, aryl, hetaryl, $C_{1-6}$-alkyl or $C_{1-6}$-alkoxy.

M may be arylene or —$CR^{27}$=$CR^{28}$—, wherein $R^{27}$ and $R^{28}$ independently from each other hydrogen or $C_{1-6}$-alkyl, optionally substituted with aryl or hetaryl.

$R^6$ and $R^7$ independently from each other may be hydrogen or $C_{1-6}$-alkyl.

$R^6$ and $R^7$ can also form —$(CH_2)_i$—U—$(CH_2)_j$—, wherein i and j independently from each other are 1, 2 or 3 and U is —O—, —S—, or a valence bond.

$R^8$ may be hydrogen or $C_{1-6}$-alkyl.

Another growth hormone secretagogue compound is represented by the structural Formula V. The chemical name of the compound of Formula V is (2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide and is represented by structural Formula V:

V

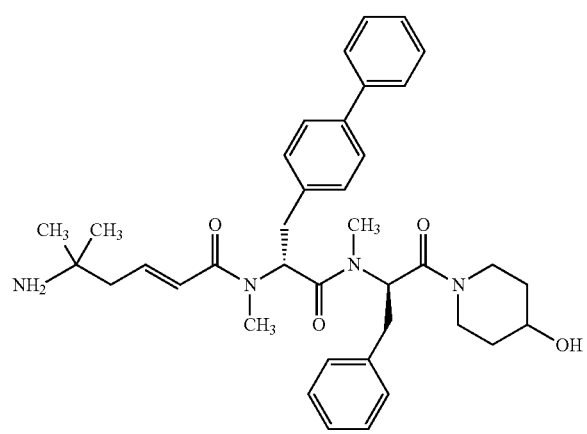

and pharmaceutically acceptable salts thereof.

Other compounds of interest include the following:

1-{(2R)-2-[N-((2E)-5-Amino-5-methylhex-2-enoyl)-N-methylamino]-3-(2-naphthyl)propionyl}-4-benzylpiperidine-4-carboxylic acid methylamide,

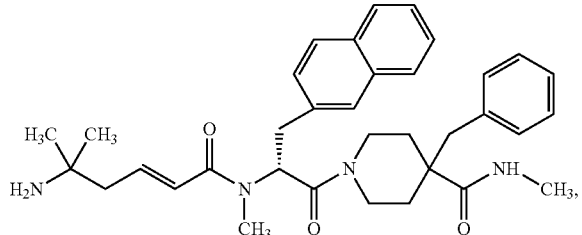

1-{(1R)-2-[N-((2E)-5-Amino-3,5-dimethylhex-2-enoyl)-N-methylamino]-3-(2-naphthyl)propionyl}-4-benzylpiperidine-4-carboxylic acid methylamide

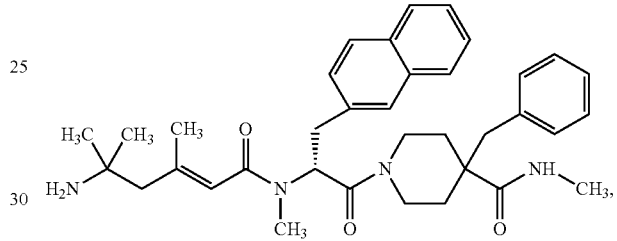

1-{(2R)-2-[N-((2E)-5-Amino-5-methylhex-2-enoyl)-N-methylamino]-3-(biphenyl-4-yl)propionyl}-4-benzylpiperidine-4-carboxylic acid methylamide

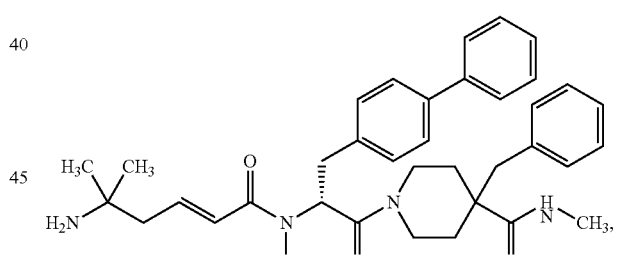

1-{(2R)-2-[N-((2E)-5-Amino-3,5-dimethylhex-2-enoyl)-N-methylamino]-3-(biphenyl-4-yl)propionyl}4-benzylpiperidine-4-carboxylic acid methylamide

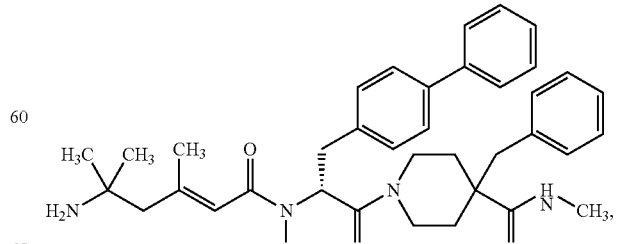

1-((2R)-2-{N-[(2E)-4-(1-Aminocyclobutyl)but-2-enoyl]-N-methylamino}-3-(biphenyl-4-yl)propionyl)-4-benzylpiperidine-4-carboxylic acid methylamide

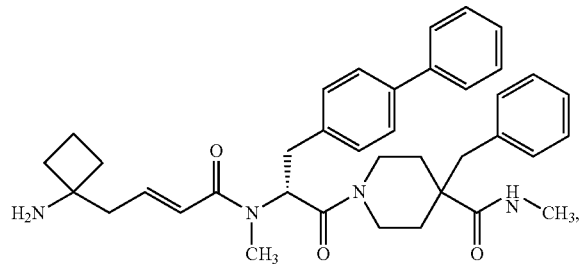 [SMILES: CNC(=O)C1(Cc2ccccc2)CCN(C(=O)[C@@H](Cc2ccc(-c3ccccc3)cc2)N(C)C(=O)/C=C/CC2(N)CCC2)CC1]

2-Amino-N-[(1R)-2-[4-benzyl-4-(N',N'-dimethylhydrazinocarbonyl)piperidin-1-yl]-1-((1H-indol-3-yl)methyl)-2-oxoethyl]-2-methylpropionamide

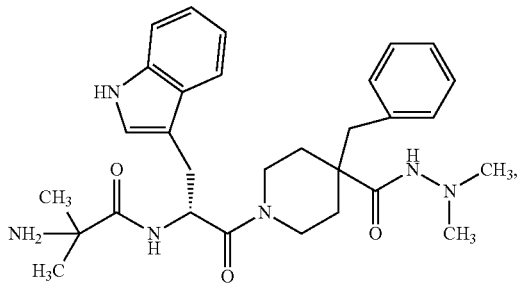 [SMILES: CN(C)NC(=O)C1(Cc2ccccc2)CCN(C(=O)[C@@H](Cc2c[nH]c3ccccc23)NC(=O)C(C)(C)N)CC1]

2-Amino-N-{(1R)-2-[(3R)-3-benzyl-3-(N',N'-dimethyl-hydrazinocarbonyl)-piperidin-1-yl]-1-benzyloxymethyl-2-oxo-ethyl}-2-methyl-propionamide

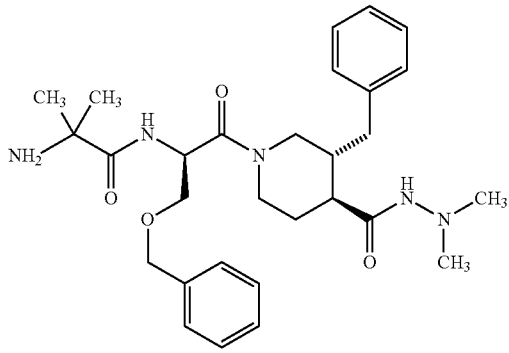 [SMILES: CN(C)NC(=O)[C@H]1CCN(C(=O)[C@@H](COCc2ccccc2)NC(=O)C(C)(C)N)C[C@@H]1Cc1ccccc1]

2-Amino-N-[(1R)-2-[(3R)-3-benzyl-3-(N'N'-dimethylhydrazinocarbonyl)-piperidin-1-yl]-1-((1H-indol-3-yl)methyl)-2-oxoethyl]-2-methylpropionamide

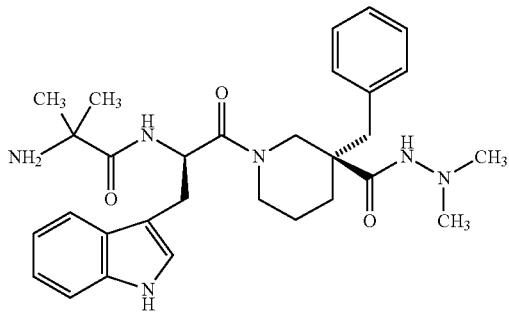 [SMILES: CN(C)NC(=O)[C@@]1(Cc2ccccc2)CCCN(C(=O)[C@@H](Cc2c[nH]c3ccccc23)NC(=O)C(C)(C)N)C1]

1-{(2R)-2-[N-((2E)-5-Amino-5-methylhex-2-enoyl)-N-methylamino]-3-(biphenyl-4-yl)propionyl}-4-benzylpiperidine-4-carboxylic acid ethyl ester

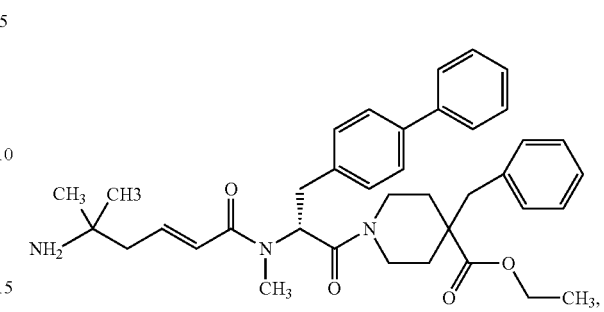

1-{(2R)-2-[N-((2E)-5-Amino-3,5-dimethylhex-2-enoyl)-N-methylamino]-3-(biphenyl-4-yl)propionyl}-4-benzylpiperidine-4-carboxylic acid ethyl ester

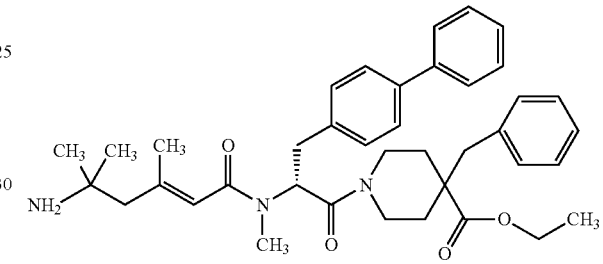

1-{(2R)-2-[N-((2E)-5-Amino-3,5-dimethylhex-2-enoyl)-N-methylamino]-3-(2-naphthyl)propionyl}-4-benzylpiperidine-4-carboxylic acid ethyl ester

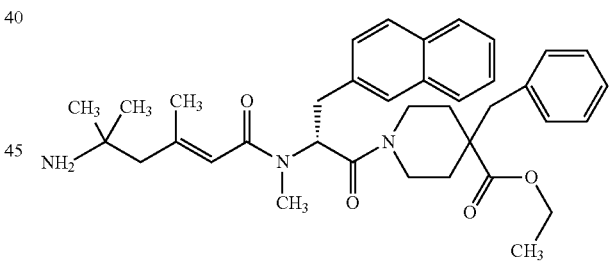

1-{(2R)-2-[N-((2E)-5-Amino-5-methylhex-2-enoyl)-N-methylamino]-3-(2-naphthyl)propionyl}-4-benzylpiperidine-4-carboxylic acid ethyl ester

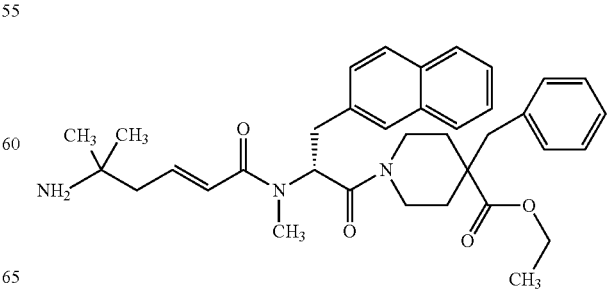

(3S)-1-[(2R)-2-((2E)-5-Amino-5-methylhex-2-enoy-
    lamino)-3-(1H-indol-3-yl) propionyl]-3-benzylpiperi-
    dine-3-carboxylic acid ethyl ester

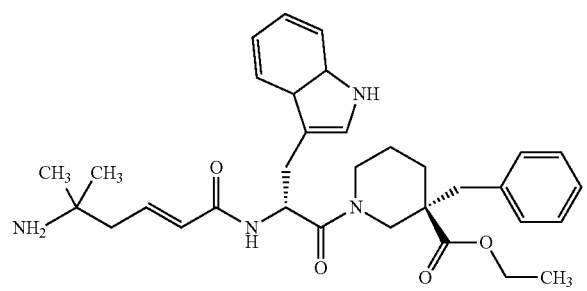 [SMILES: CCOC(=O)[C@]1(Cc2ccccc2)CCCN(C(=O)[C@@H](CC2=CNC3C=CC=CC23)NC(=O)/C=C/CC(C)(C)N)C1]

(3S)-1-[(2R)-2-((2E)-5-Amino-3,5-dimethylhex-2-enoy-
    lamino)-3-(1H-indol-3-yl)propionyl]-3-benzylpiperidine-
    3-carboxylic acid ethyl ester

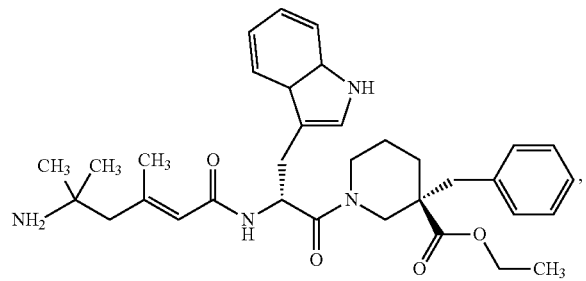 [SMILES: CCOC(=O)[C@]1(Cc2ccccc2)CCCN(C(=O)[C@@H](CC2=CNC3C=CC=CC23)NC(=O)/C=C(\C)CC(C)(C)N)C1]

(3S)-1-[(2R)-2-(3-(Aminomethyl)benzoylamino)-3-(1H-in-
    dol-3-yl)propionyl]-3-benzylpiperidine-3-carboxylic acid
    ethyl ester

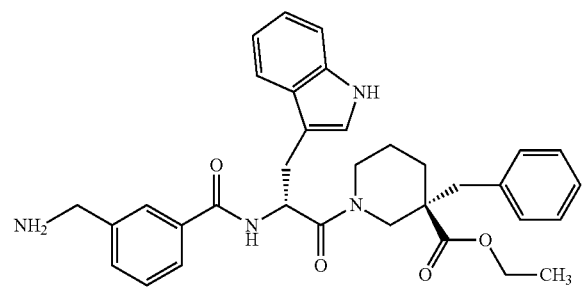 [SMILES: CCOC(=O)[C@]1(Cc2ccccc2)CCCN(C(=O)[C@@H](Cc2c[nH]c3ccccc23)NC(=O)c2cccc(CN)c2)C1]

(2E)-5-Amino-5-methylhex-2-enoic acid N-{(1R)-2-[4-ben-
    zyl-4-(N',N'-dimethyl-hydrazinocarbonyl)piperidin-1-
    yl]-1-((2-naphthyl)methyl)-2-oxoethyl}-N-methylamide

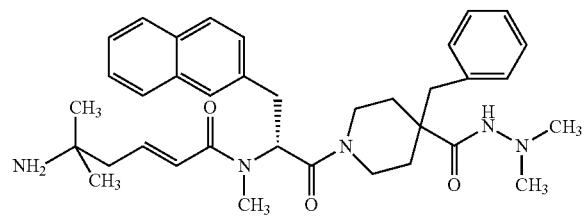 [SMILES: CN(C)NC(=O)C1(Cc2ccccc2)CCN(C(=O)[C@@H](Cc2ccc3ccccc3c2)N(C)C(=O)/C=C/CC(C)(C)N)CC1]

(2E)-5-Amino-5-methylhex-2-enoic acid N-[(1R)-2-[3-ben-
    zyl-3-(N',N'-dimethyl-hydrazinocarbonyl)-piperidin-1-
    yl]-1-((1H-indol-3-yl)methyl)-2-oxoethyl]amide

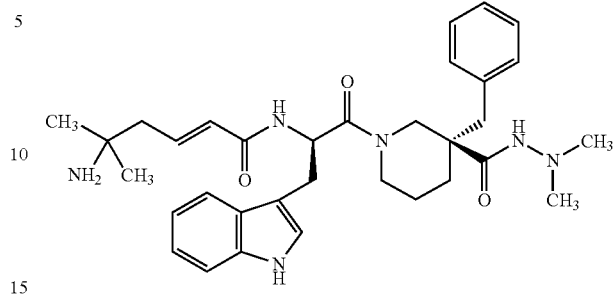

(2E)-5-Amino-5-methylhex-2-enoic acid N-{(1R)-2-[3-ben-
    zyl-3-(N',N'-dimethyl-hydrazinocarbonyl)-piperidin-1-
    yl]-1-(2-naphthyl)methyl)-2-oxoethyl}-N-methyl-amide

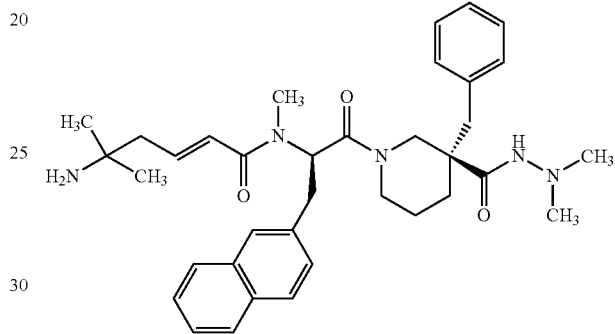

2E)-5-Amino-5-methylhex-2-enoic acid {(1R)-2-[3-benzyl-
    3-N',N'-dimethyl-hydrazinocarbonyl)piperidin-1-yl]-1-
    (benzyloxymethyl)-2-oxoethyl}amide

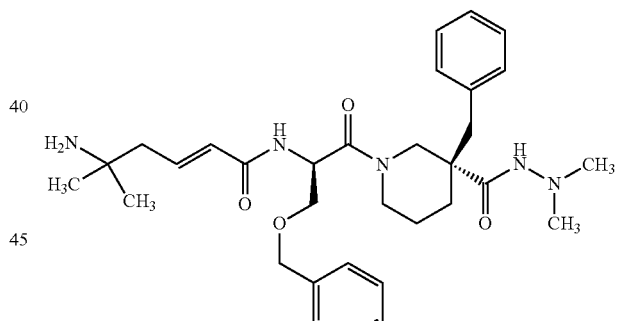

2-Amino-N-{2-[3-benzyl-3-(N',N'-dimethylhydrazinocar-
    bonyl)piperidin-1-yl]-1-((2-naphthyl)methyl)-2-oxo-
    ethyl}-2-methyl-propionamide

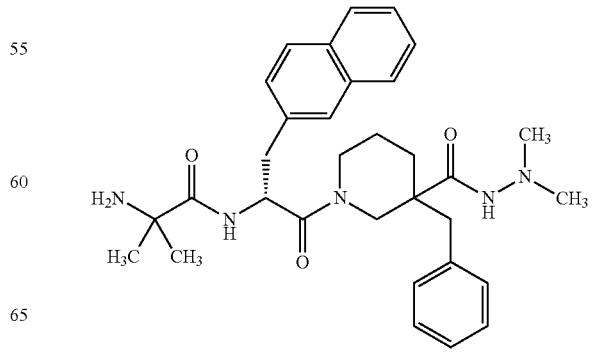

23

2-Amino-N-{(1R)-2-[3-benzyl-3-(N',N'-dimethylhydrazinocarbonyl)piperidin-1-yl]-1-((biphenyl-4-yl)methyl)-2-oxoethyl}-2-methylpropionamide

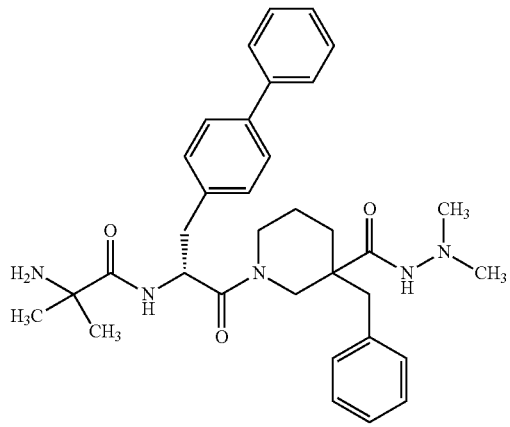 [SMILES: CN(C)NC(=O)C1(Cc2ccccc2)CCCN(C(=O)[C@@H](Cc2ccc(-c3ccccc3)cc2)NC(=O)C(C)(C)N)C1]

2-Amino-N-{(1R)-2-[3-benzyl-3-(N',N'-dimethylhydrazinocarbonyl)piperidin-1-yl]-1-((1H-indol-3-yl)methyl)-2-oxoethyl}-2-methylpropionamide

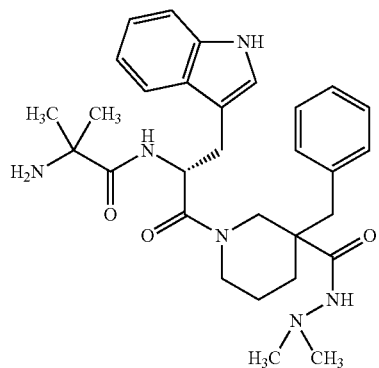 [SMILES: CN(C)NC(=O)C1(Cc2ccccc2)CCCN(C(=O)[C@@H](Cc2c[nH]c3ccccc23)NC(=O)C(C)(C)N)C1]

2-Amino-N-{2-[3-benzyl-3-(N'-dimethylhydrazinocarbonyl)piperidin-1-yl]-1-(benzyloxymethyl)-2-oxoethyl}-2-methylpropionamide

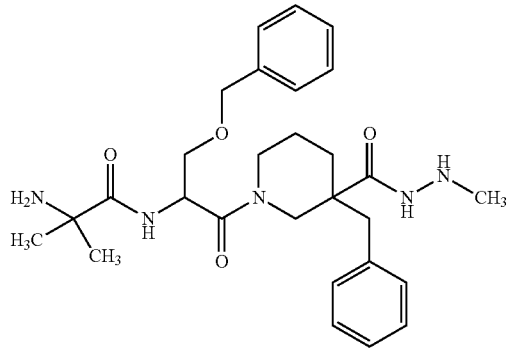 [SMILES: CNNC(=O)C1(Cc2ccccc2)CCCN(C(=O)C(COCc2ccccc2)NC(=O)C(C)(C)N)C1]

24

2-Amino-N-{(1R-2-[3-benzyl-3-(N',N'-dimethylhydrazinocarbonyl)piperidin-1-yl]-1-(benzyloxymethyl)-2-oxoethyl}-2-methylpropionamide

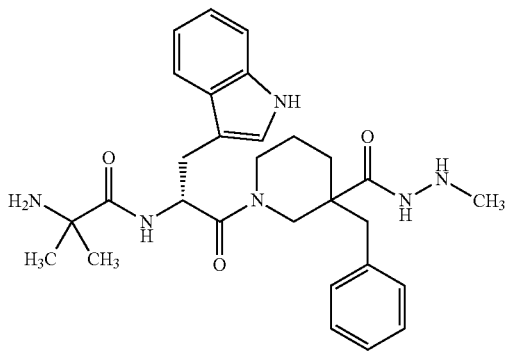 [SMILES: CNNC(=O)C1(Cc2ccccc2)CCCN(C(=O)[C@@H](Cc2c[nH]c3ccccc23)NC(=O)C(C)(C)N)C1]

1-[(2R)-2-(2-Amino-2-methylpropionylamino)-3-(1-H-indol-3-yl)propionyl]-3-benzylpiperidine-3-carboxylic acid (pyrrolidin-1-yl)amide

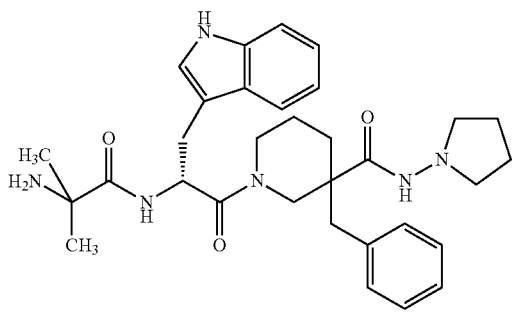 [SMILES: CC(C)(N)C(=O)N[C@H](Cc1c[nH]c2ccccc12)C(=O)N1CCCC(Cc2ccccc2)(C(=O)NN2CCCC2)C1]

(2E)-5-Amino-5-Methylhex-2-enoic acid N-((1R)-1-{N-[(1R)-1-benzyl-2-(4-((dimethylamino)methyl)piperidin-1-yl)-2-oxoethyl]-N-methylcarbamoyl}-2-(2-naphthyl)ethyl)-N-methylamide

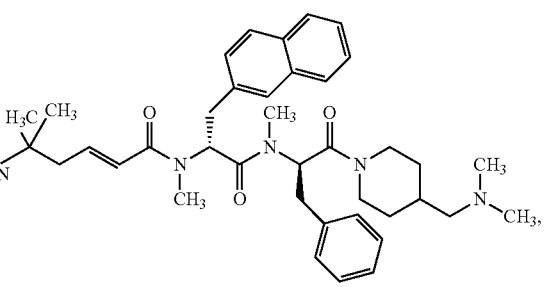

(2E)-5-Amino-5-Methylhex-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide N-((1R)-1-{N-[(1R)-1-Benzyl-2-((2S)-2-((dimethylamino)methyl)pyrrolidin-1-yl)-2-oxoethyl]-N-methylcarbamoyl}-2-(2-naphthyl)ethyl)-N-methyl-3-((methylamino)methyl)benzamide

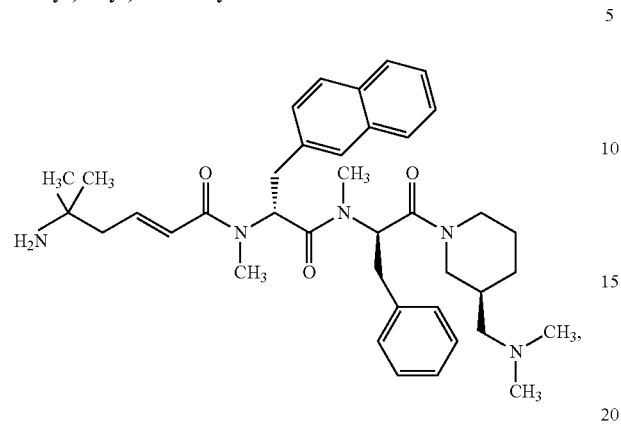

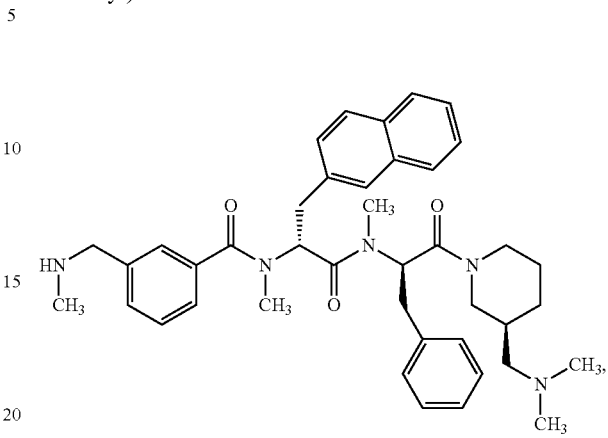

(2E)-4-(1-Aminocyclobutyl)but-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide (2E)-5-Amino-5-methylhex-2enoic acid N-((1R-1-{N-[(1R)-1-benzyl-2-(4-(dimethylamino)piperidin-1-yl)-2-oxoethyl]-N-methylcarbamoyl}-2-(2-naphthyl)ethyl)-N-methylamide.

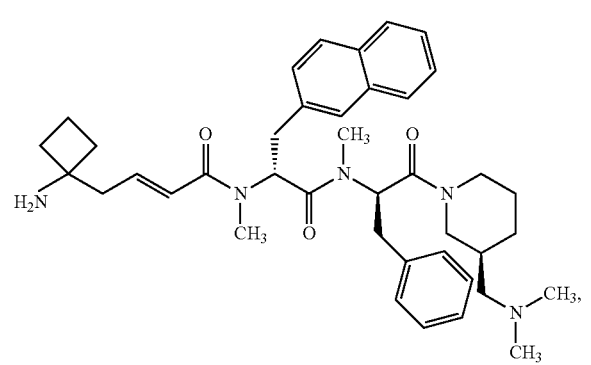 [SMILES: CN(C)C[C@@H]1CCCN(C(=O)[C@@H](Cc2ccccc2)N(C)C(=O)[C@@H](Cc2ccc3ccccc3c2)N(C)C(=O)/C=C/CC2(N)CCC2)C1]

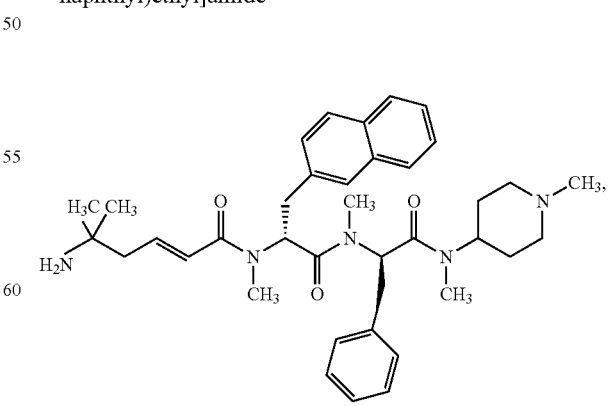

(2E)-5-Amino-5-methylhex-2-enoic acid N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylamide (2E)-5-Amino-5-methylhex-2-enoic acid N-methyl-N-[(1R)-1-(N-methyl-N-{(1R)-1-[N-methyl-N-(1-methylpiperidin-4-yl)carbamoyl]-2-phenylethyl}carbamoyl)-2-(2-naphthyl)ethyl]amide

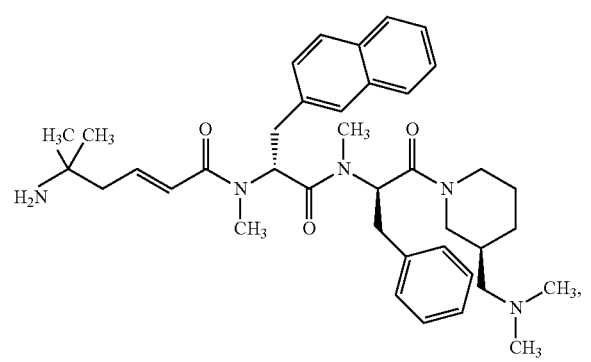 [SMILES: CN(C)C[C@@H]1CCCN(C(=O)[C@@H](Cc2ccccc2)N(C)C(=O)[C@@H](Cc2ccc3ccccc3c2)N(C)C(=O)/C=C/CC(C)(C)N)C1]

27

3-Aminomethyl-N-((1R)-1-{N-[(1R)-1-benzyl-2-(4-methylpiperazin-1-yl)-2-oxoethyl]-methylcarbamoyl}-2-(2-naphthyl)ethyl)-N-methylbenzamide

28

3-Aminomethyl-N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)benzamide

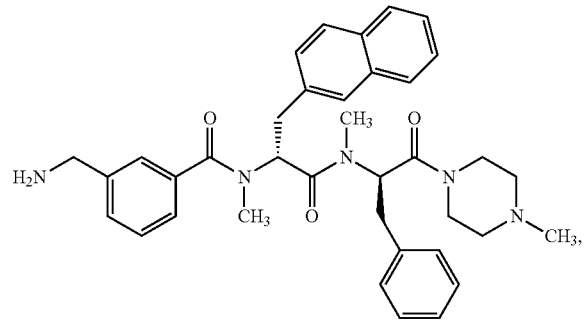 [SMILES: CN1CCN(C(=O)[C@@H](Cc2ccccc2)N(C)C(=O)[C@@H](Cc2ccc3ccccc3c2)N(C)C(=O)c2cccc(CN)c2)CC1]

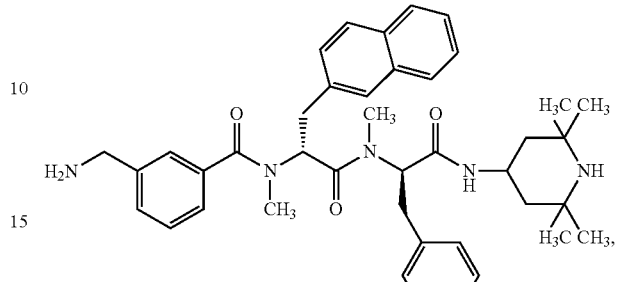

(2E)-5-Amino-5-methylhex-2-enoic acid N-((1R)-1-{N-[(1R)-1-benzyl-2-(4-methylpiperazin-1-yl)-2-oxoethyl]-N-methylcarbamoyl}-2-(2-naphthyl)-N-methylamide (2E)-5-Amino-3,5-dimethylhex-2-enoic acid N-methyl-N-((1R-1-{N-methyl-N-[(1R)-2-phenyl-1-((2,2,6,6-tetramethylpiperidin-4-yl)carbamoyl)ethyl]carbamoyl}-2-(2-naphthyl)ethyl)amide

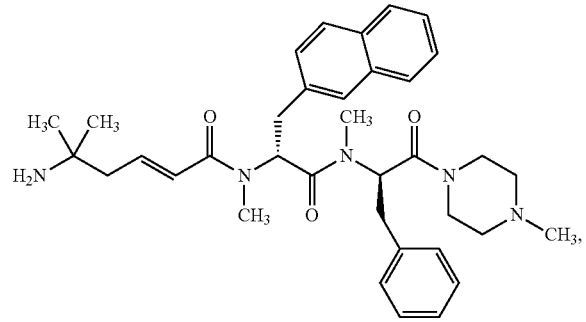 [SMILES: CN1CCN(C(=O)[C@@H](Cc2ccccc2)N(C)C(=O)[C@@H](Cc2ccc3ccccc3c2)N(C)C(=O)/C=C/CC(C)(C)N)CC1]

(2E)-5-Amino-5-methylhex-2-enoic acid N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)amide (2E)-4-(1-Aminocyclobutyl)but-2-enoic acid N-((1R)1-{N-[(1R)1-benzyl-2-(4-methylpiperazin-1-yl)-2-oxoethyl]-N-methylcarbamoyl}-2-(2-naphthyl)ethyl)-N-methylamide

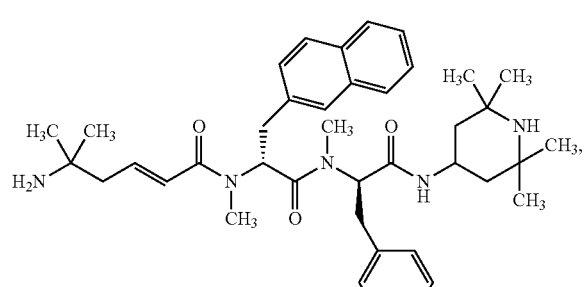

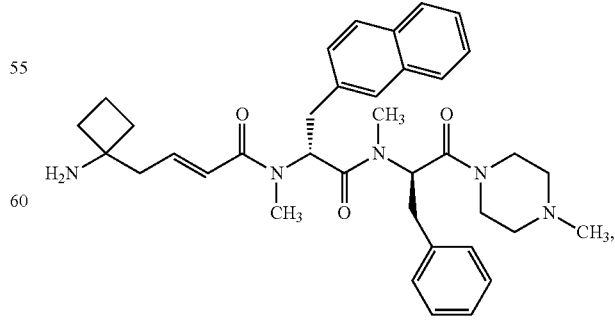

(2E)-5-Amino-3,5-dimethylhex-2-enoic acid N-((1R)1-{N-[(1R)1-benzyl-2-(4-methylpiperazin-1-yl)-2-oxoethyl]-N-methylcarbamoyl}-2-(2-naphthyl)ethyl)-N-methylamide

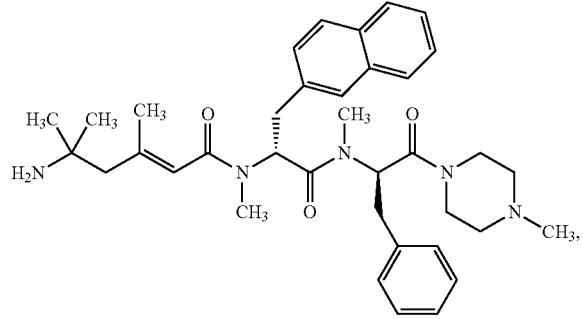 [SMILES: C/C(=C\C(=O)N(C)[C@H](Cc1ccc2ccccc2c1)C(=O)N(C)[C@H](Cc1ccccc1)C(=O)N1CCN(C)CC1)CC(C)(C)N]

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

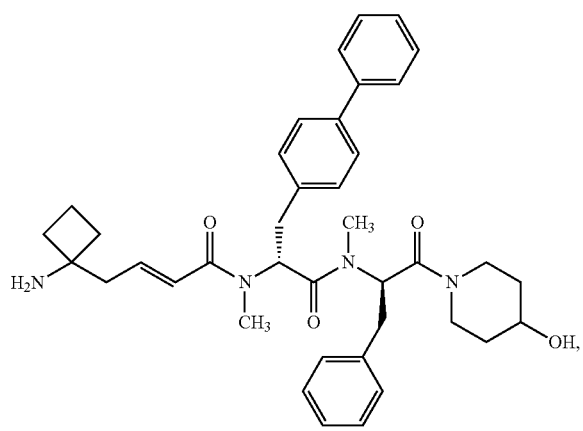 [SMILES: CN(C(=O)/C=C/CC1(N)CCC1)[C@H](Cc1ccc(-c2ccccc2)cc1)C(=O)N(C)[C@H](Cc1ccccc1)C(=O)N1CCC(O)CC1]

(2E)-5-Amino-3,5-dimethylhex-2enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

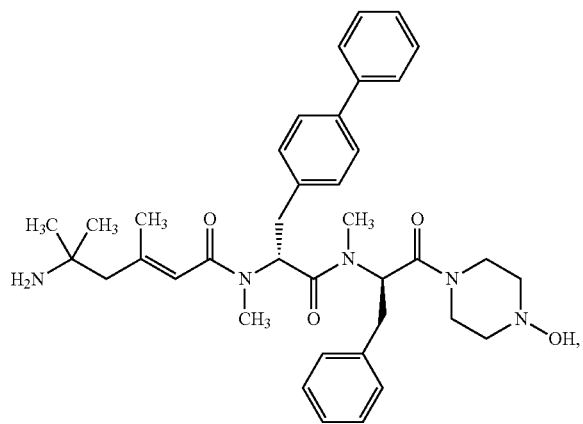 [SMILES: C/C(=C\C(=O)N(C)[C@H](Cc1ccc(-c2ccccc2)cc1)C(=O)N(C)[C@H](Cc1ccccc1)C(=O)N1CCN(O)CC1)CC(C)(C)N]

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

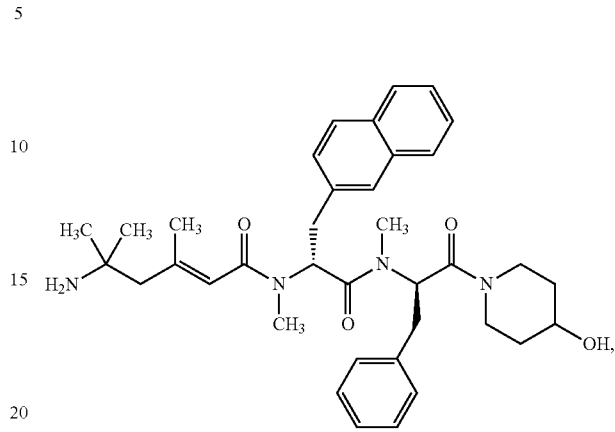

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

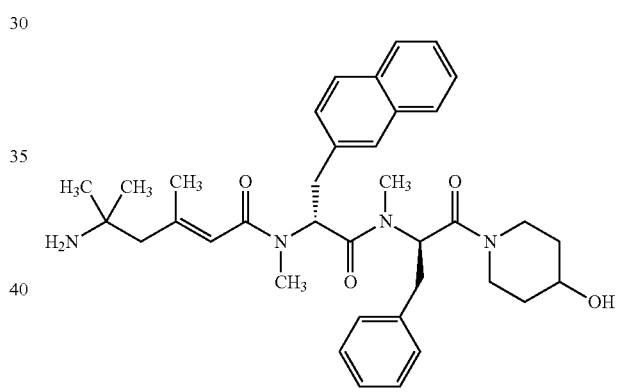

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

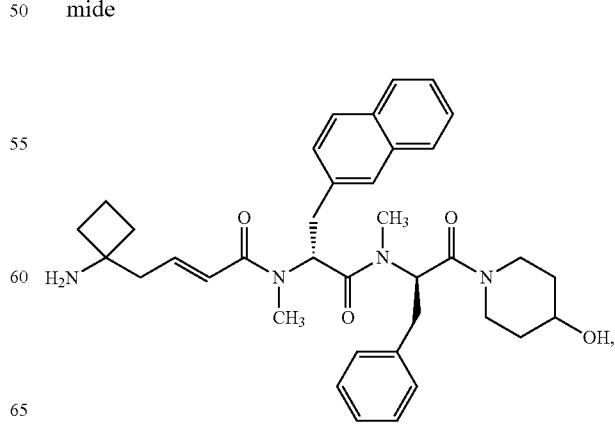

(2E)-5-Amino-5-methylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide (2E)-5-Amino-5-methylhex-2-enoic acid N-((1R)-1-{N-[(1R)-1-(3-hydroxycyclohexylcarbamoyl)-2-phenylethyl]-N-methylcarbamoyl}-2-(2-naphthyl)ethyl)-N-methylamide

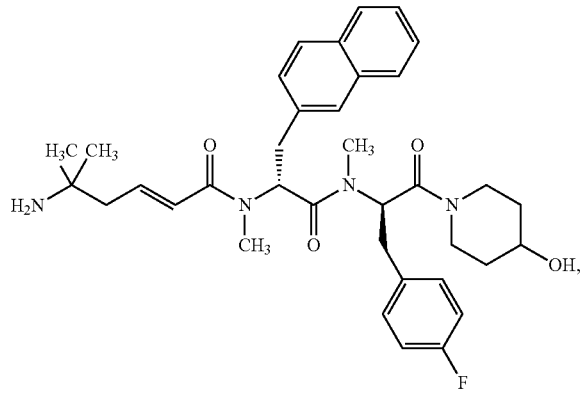 [SMILES: CN(C(=O)/C=C/CC(C)(C)N)[C@H](Cc1ccc2ccccc2c1)C(=O)N(C)[C@H](Cc1ccc(F)cc1)C(=O)N1CCC(O)CC1]

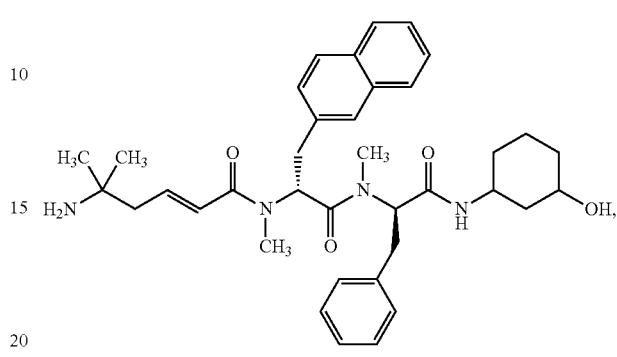

(2E)-5-Amino-3,5-dimethylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide (2E)4-(1-Aminocyclobutyl)but-2-enoic acid N-((1R)-1-{N-[(1R)-1-benzyl-2-(4-(dimethylamino)piperidin-1-yl)-2-oxoethyl]-N-methylcarbamoyl}-2-(2-naphthyl)ethyl)-N-methylamide

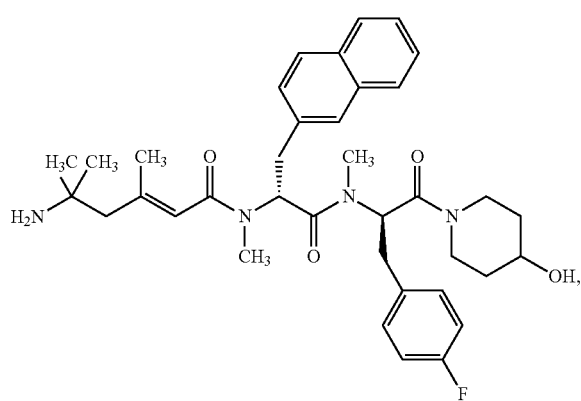 [SMILES: C/C(=C\C(=O)N(C)[C@H](Cc1ccc2ccccc2c1)C(=O)N(C)[C@H](Cc1ccc(F)cc1)C(=O)N1CCC(O)CC1)CC(C)(C)N]

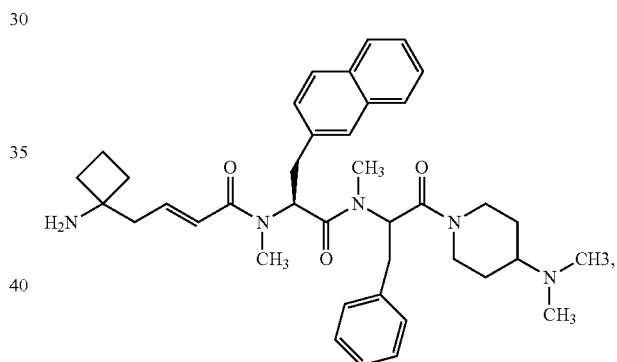

(2E)-5-Amino-5-methylhex-2-enoic acid N-((1R)-1-{N-[(1R)-1-benzyl-2-(4-hydroxy-4-(2-thienyl)piperidin-1-yl)-2-oxoethyl]-N-methylcarbamoyl}-2-(2-naphthyl)ethyl)-N-methylamide (2E)-5-Amino-5-methylhex-2-enoic acid N-((1R)-1-{N-[(2R)-2-(4-hydroxypiperidin-1-yl)-2-oxo-1-((2-thienyl)methypethyl]-N-methylcarbamoyl}-2-(2-naphthyl)ethyl)-N-methylamide

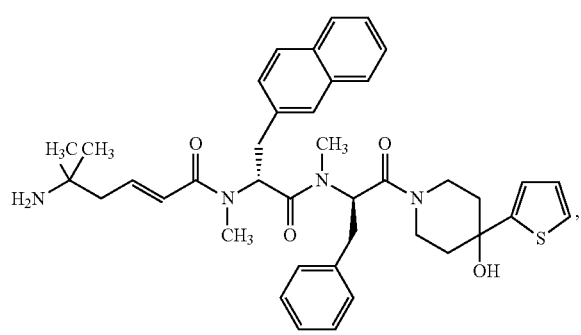 [SMILES: CN(C(=O)/C=C/CC(C)(C)N)[C@H](Cc1ccc2ccccc2c1)C(=O)N(C)[C@H](Cc1ccccc1)C(=O)N1CCC(O)(c2cccs2)CC1]

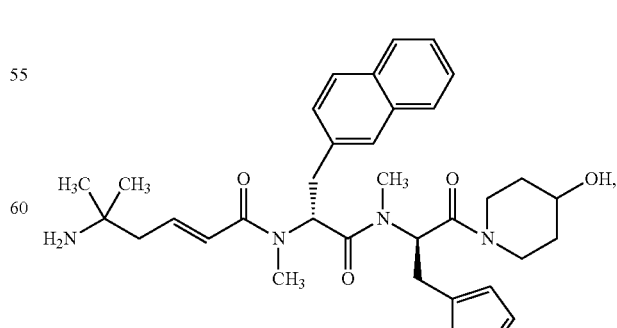

33

(2E)-5-Amino-3,5-dimethylhex-2-enoic acid N-((1R)-1-{N-[((2R)-2-(4-hydroxypiperidin-1-yl)-2-oxo-1-((2-thienyl)methyl)ethyl]-N-methylcarbamoyl}-2-(2-naphthyl)ethyl)-N-methylamide

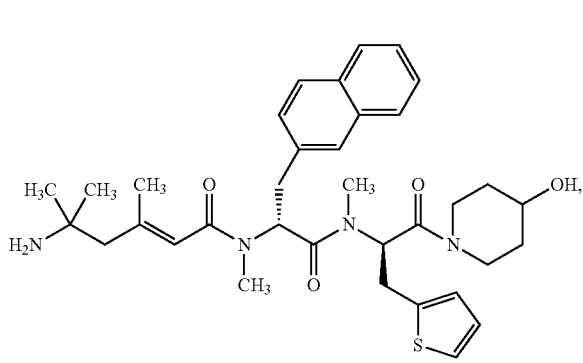 [SMILES: C/C(=C\C(=O)N(C)[C@H](Cc1ccc2ccccc2c1)C(=O)N(C)[C@H](Cc1cccs1)C(=O)N1CCC(O)CC1)CC(C)(C)N]

(2E)-5-Amino-5-methylhex-2-enoic acid N-((1R)-2-(biphenyl-4-yl)-1-{N-[(2R)-2-(4-hydroxypiperidin-1-yl)-2-oxo-1-((2-thienyl)methyl)ethyl]-N-methylcarbamoyl}ethyl)-N-methylamide

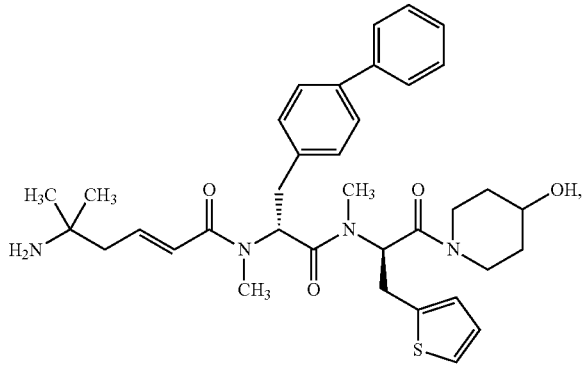 [SMILES: CN(C(=O)/C=C/CC(C)(C)N)[C@H](Cc1ccc(-c2ccccc2)cc1)C(=O)N(C)[C@H](Cc1cccs1)C(=O)N1CCC(O)CC1]

(2E)-5-Amino-3,5-dimethylhex-2-enoic acid N-((1R)-2-(biphenyl-4-yl)-1-{N-[(1R)-2-(4-hydroxypiperidin-1-yl)-2-oxo-1-((2-thienyl)methyl)ethyl]-N-methylcarbamoyl}ethyl)-N-methylamide

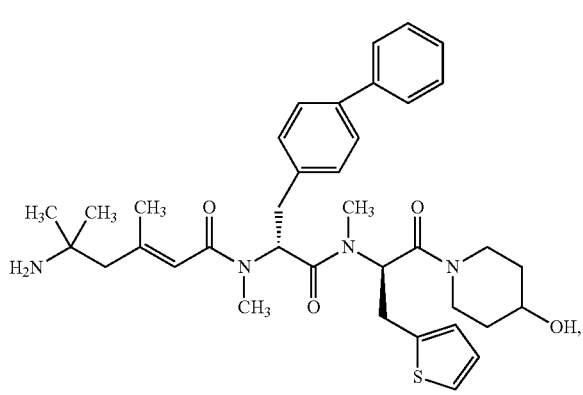 [SMILES: C/C(=C\C(=O)N(C)[C@H](Cc1ccc(-c2ccccc2)cc1)C(=O)N(C)[C@H](Cc1cccs1)C(=O)N1CCC(O)CC1)CC(C)(C)N]

34

(2E)-5-Methyl-5-(methylamino)hex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

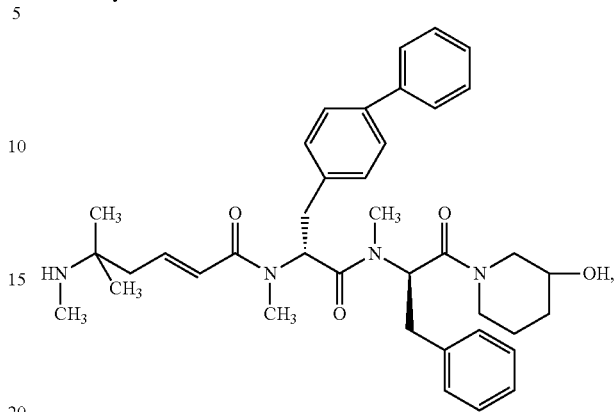

(2E)-4-(1-Aminocyclobutyl)but-2-enoic acid ((1R)-1-{N-[(1R)-1-benzyl-2-(4-hydroxypiperidin-1-yl)-2-oxoethyl]-N-methylcarbamoyl}-2-(biphenyl-4-yl)ethyl)amide

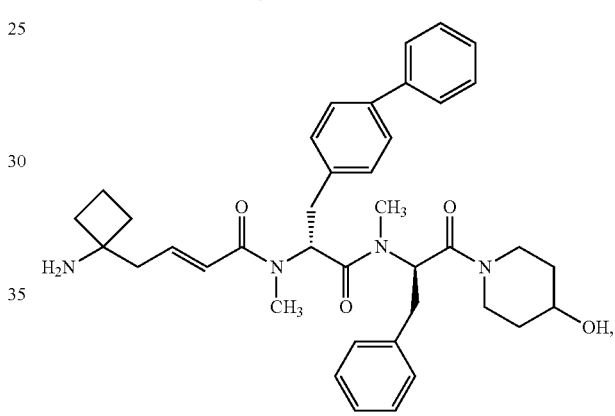

and pharmaceutically acceptable salts thereof.

Another growth hormone secretagogue is represented by structural Formula VI or a pharmaceutically acceptable salt, solvate or hydrate thereof. The chemical name for the compound represented by structural Formula VI is: (2E)-4-(1-aminocyclobutyl)but-2-enoic acid N-((1R)-1-{N-[(1R)-1-benzyl-2-(4-hydroxypiperidin-1-yl)-2-oxoethyl]-N-methylcarbomoyl}-2-(biphenyl-4-yl)ethyl)-N-methylamide.

VI

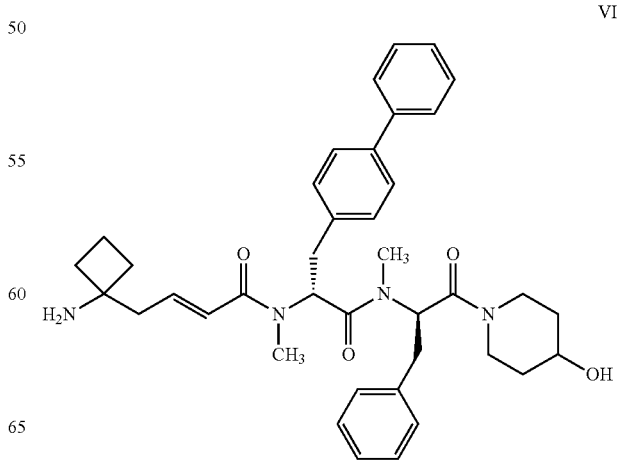

Another growth hormone secretagogue is represented by structural Formula VII or a pharmaceutically acceptable salt, solvate or hydrate thereof. The chemical name of the compound represented by structural Formula VII is: (2E)-5-amino-5-methylhex-2-enoic acid N-methyl-N-((1R)-1-{N-methyl-N-[(1R)-2-phenyl-1-(N,N',N'-trimethylhydrazinocarbonyl)ethyl]carbamoyl}-2-(2-naphthyl)ethyl)amide.

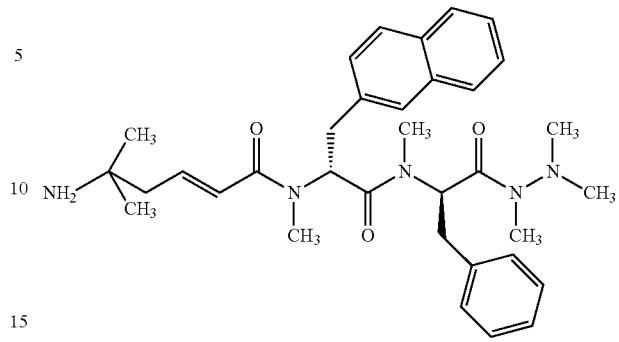

VIII

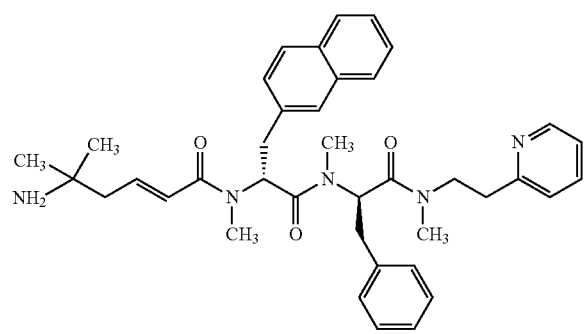

VII

Another growth hormone secretagogue is represented by structural Formula VIII or a pharmaceutically acceptable salt, solvate or hydrate thereof.

The chemical name of the compound represented by structural Formula VIII is: (2E)-5-amino-5-methylhex-2-enoic acid N-methyl-N-((1R)-1-{N-methyl-N-[(1R)-2-phenyl-1-(N,N',N'-trimethylhydrazinocarbonyl)ethyl]carbamoyl}2-(2-naphthyl)ethyl)amide.

Another the growth hormone secretagogue is represented by structural Formula IX or a pharmaceutically acceptable salt, solvate or hydrate thereof. The chemical name for the compound represented by structural Formula IX is: 2-amino-N-(2-(2-(N-((2R)-2-(N-((2E)-5-amino-5-methylhex-2-enoyl)-N-methylamino)-3-(2-napthyl)propionyl)-N-methylamino)ethyl)phenyl)acetamide.

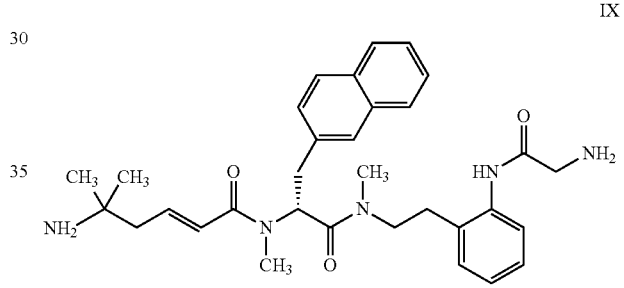

IX

Further exemplary growth hormone secretagogues can be selected from GHRP-1 (Formula X), GHRP-2 (Formula XI), GHRP-6 (Formula XII), NN703 (Formula XIII), Ipamorelin (Formula XIV), Capromorelin (Formula XV) and MK-677 (Formula XVI) and analogs of any of the above.

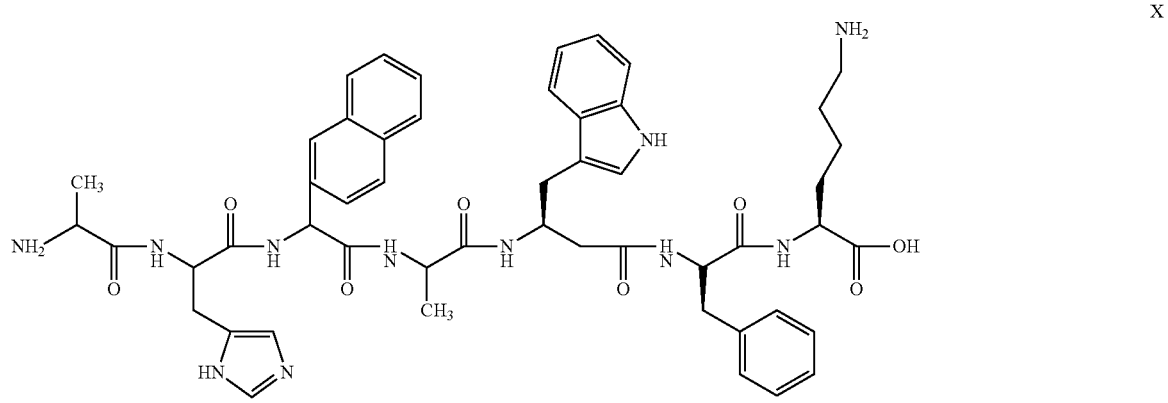

X

XI

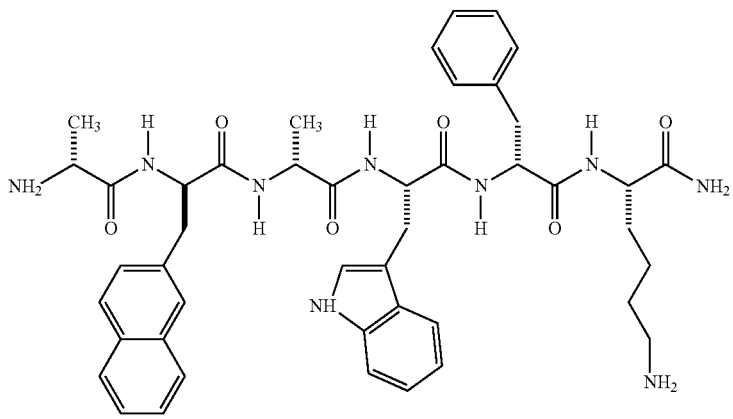

XII

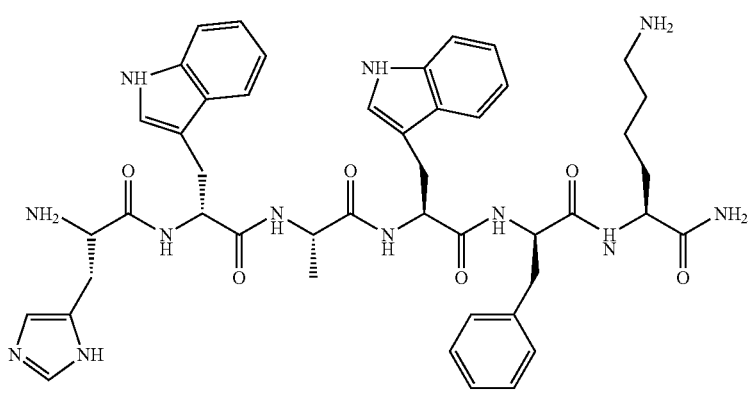

XIII

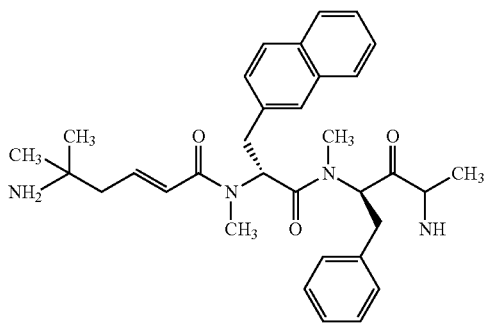

XIV

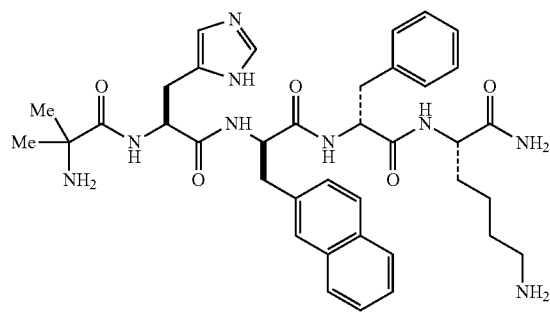

XV

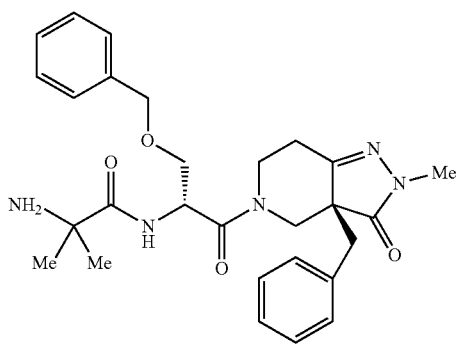

XVI

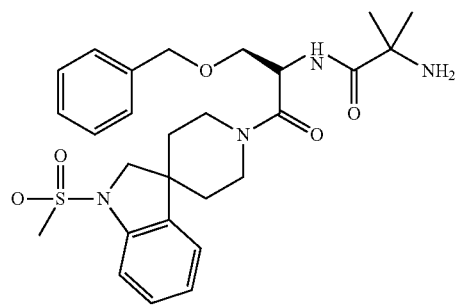

As used herein, the terms "emetic syndrome", "emetic condition" "vomiting", "nausea" and "emesis" are used interchangeably and intended to have the same meaning. Emetic syndromes are those characterized by the reflexive act of ejecting the contents of the stomach through the mouth, or the feeling that such a reflexive action is likely to occur. Emetic conditions are often associated with chemotherapeutic treatment (chemotherapy-induced nausea and vomiting (CINV)) or surgery (post-operative nausea and vomiting (PONV)). Emetic syndromes resulting from chemotherapeutic treatment can be classified into three types (1) acute, (2) delayed, and (3) anticipatory. Acute emesis occurs within about 24 hours of receiving chemotherapy, and delayed emesis occurs between about 24 hours and about 120 hours of receiving chemotherapy (Grunberg et al. (2004) *Cancer* 100:2261-8).

As used herein, the term "cancer symptom burden" is used as a measure of a cancer subjects quality of life or the amount of ameloriation of advanced cancer symptoms. In one embodiment, a subject's cancer symptom burden is measured by the Anderson Symptom Assessment System (ASAS).

The severity of overall cancer symptom burden or emetic conditions can be characterized by a number of scales that are known in the art. For example, the Anderson Symptom Assessment System (ASAS) is a modified form of the Edmonton Symptom Assessment System that includes an assessment of pain, fatigue, nausea, depression, anxiety, drowsiness, shortness of breath, appetite, sleep and feeling of wellbeing (see, Palmer et al. (2005) *J. Pain and Symptom Management* 6:565-571). ASAS requires patients to identify the severity of each of these symptoms on a 0-10 scale, with 0=none (or best), and 10=most (or worst imaginable). A subjects ASAS score is the sum total of their numerical answers for the ten symptoms.

Alternatively, the Hesketh scale can be used to classify the acute emetoenicity of cancer chemotherapy (Hesketh et al. (1997) *J. Clin. Oncology* 15:103-109). The Hesketh scale sets forth five levels of emetogenicity. Level 1 consists of agents that are nonemetogenic; Level 2 consists of agents that cause vomiting in 10-30% of patients; Level 3 consists of agents that are moderately emetogenic with 30-60% of patients experiencing emesis; Level 4 consists of agents that produce emesis in 60-90% of patients; and Level 5 consists of agents that cause vomiting in >90% of patients.

"Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species. In a preferred embodiment, the mammal is a human.

As used herein, "treating" and "treatment" refer to treating, reducing or preventing emesis in a subject.

As used herein, "therapeutically effective amount" refers to an amount sufficient to elicit the desired biological response. In the present invention, the desired biological response is treating or preventing emesis.

The therapeutically effective amount or dose will depend on the age, sex and weight of the patient, and the current medical condition of the patient. The skilled artisan will be able to determine appropriate dosages depending on these and other factors to achieve the desired biological response.

A suitable dose per day for the growth hormone secretagogue can be in the range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000 mg, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg.

Other suitable doses per day for the growth hormone secretagogue include doses of about or greater than 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 µg, about 100 µg, about 200 µg, about 300 µg, about 400 µg, about 500 µg (0.5 mg), about 1 mg, about 1.25 mg, about 1.5 mg, about 2.0 mg, about 2.5 mg, about 3.0 mg, about 3.5 mg, about 4.0 mg, about 4.5 mg, about 5 mg, about 10 mg, about 20 mg, about 30 mg, about 40 mg, about 50 mg, about 100 mg, about 200 mg, about 300 mg, about 400 mg, about 500 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg.

A suitable dose of the growth hormone secretagogue can be in the range of from about 1-150 mg per day, such as from about 10 mg to about 100 mg, for example, from about 20 mg to about 80 mg, such as about 30 mg to about 60 mg per day, such as about 50 mg per day. The dose can be administered in a single dosage or in multiple dosages, for example from 1 to 4 or more times per day. When multiple dosages are used, the amount of each dosage can be the same or different.

A suitable dose for the additional therapeutic agent can be in same range as described above for the growth hormone secretagogue. The dose of growth hormone secretagogue and additional agent can be the same or different. Suitable doses for the additional agents can be found in the literature.

Administration

Administration can take place as necessary to prevent or treat an emetic condition. Administration of a growth hormone secretagogue can take place prior to, after or at the same time as a chemotherapeutic agent that is likely to cause nausea or vomiting.

Pharmaceutical Compositions and Modes of Administration

The growth hormone secretagogue (also referred to herein as "active compounds") of the invention can be incorporated into pharmaceutical compositions. Such compositions typically include the growth hormone secretagogue and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

The pharmaceutical compositions can be included in a container, pack, or dispenser together with instructions for administration.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. The compounds for use in the method of the invention can be formulated for administration by any suitable route, such as for oral or parenteral, for example, transdermal, transmucosal (e.g., sublingual, lingual, (trans)buccal), vaginal (e.g., trans- and perivaginally), (intra)nasal and (trans)rectal), subcutaneous, intramuscular, intradermal, intra-arterial, intravenous, inhalation, and topical administration. In preferred embodiments of the invention, the growth hormone secretagogues are administered orally.

Suitable compositions and dosage forms include tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays, dry powders or aerosolized formulations.

It is preferred that the compounds are orally administered. Suitable oral dosage forms include, for example, tablets, capsules or caplets prepared by conventional means with pharmaceutically acceptable excipients such as binding agents (e.g., polyvinylpyrrolidone or hydroxypropylmethylcellulose); fillers (e.g., lactose, microcrystalline cellulose or calcium phosphate); lubricants (e.g., magnesium stearate, talc or silica); disintegrates (e.g., sodium starch glycollate); or wetting agents (e.g., sodium lauryl sulphate). If desired, the tablets can be coated, e.g., to provide for ease of swallowing or to provide a delayed release of active, using suitable methods. Liquid preparation for oral administration can be in the form of solutions, syrups or suspensions. Liquid preparations (e.g., solutions, suspensions and syrups) are also suitable for oral administration and can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

As used herein, the term "pharmaceutically acceptable salt" refers to a salt of a compound to be administered prepared from pharmaceutically acceptable non-toxic acids including inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

The growth hormone secretagogues disclosed can be prepared in the form of their hydrates, such as hemihydrate, monohydrate, dihydrate, trihydrate, tetrahydrate and the like and as solvates.

It is understood that growth hormone secretagogue compounds can be identified, for example, by screening libraries or collections of molecules using suitable methods. Another source for the compounds of interest are combinatorial libraries which can comprise many structurally distinct molecular species. Combinatorial libraries can be used to identify lead compounds or to optimize a previously identified lead. Such libraries can be manufactured by well-known methods of combinatorial chemistry and screened by suitable methods.

Stereochemistry

Many of the compounds described herein can have one or more chiral centers and therefore can exist in different enantiomeric forms. If desired, a chiral carbon can be designated with an asterisk (*). When bonds to the chiral carbon are depicted as straight lines in the formulas of the invention, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When a compound of the present invention has two or more chiral carbons, it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers which are not mirror-images (e.g., (S,S) and (R,S)) are diastereomers. The diastereoisomeric pairs may be separated, by methods known to those skilled in the art, for example chromatography or crystallization and the individual enantiomers within each pair may be separated as described above. The present invention includes each diastereoisomer of such compounds and mixtures thereof.

VARIABLE DEFINITIONS

In the above structural formulas and throughout the present specification, the following terms have the indicated meanings:

The $C_{1-6}$-alkyl, $C_{1-6}$-alkylene, $C_{1-4}$-alkyl or $C_{1-4}$-alkylene groups specified above are intended to include those alkyl or alkylene groups of the designated length in either a linear or branched or cyclic configuration as permitted. Examples of linear alkyl are methyl, ethyl, propyl, butyl, pentyl, and hexyl and their corresponding divalent moieties, such as ethylene. Examples of branched alkyl are isopropyl, sec-butyl, tert-butyl, isopentyl, and isohexyl and their corresponding divalent moieties, such as isopropylene. Examples of cyclic alkyl are $C_{3-6}$-cycloalkyl such as cyclopropyl, cyclobutyl, cyclopentyl and cyclohexyl and their corresponding divalent moieties, such as cyclopropylene.

The $C_{1-6}$-alkoxy groups specified above are intended to include those alkoxy groups of the designated length in either a linear or branched or cyclic configuration. Examples of linear alkoxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are cyclopropyloxy, cyclobutyloxy, cyclopentyloxy and cyclohexyloxy.

The $C_{1-7}$-acyl groups specified above are intended to include those acyl groups of the designated length in either a linear or branched or cyclic configuration. Examples of linear acyl are formyl, acetyl, propionyl, butyryl, valeryl, etc. Examples of branched are isobutyryl, isovaleryl, pivaloyl, etc. Examples of cyclic are cyclopentylcarbonyl, cyclohexylcarbonyl, etc.

In the present context, the term "aryl" is intended to include monovalent carbocyclic aromatic ring moieties, being either monocyclic, bicyclic or polycyclic, e.g., phenyl and napthyl, optionally substituted with one or more $C_{1-6}$alkyl, $C_{1-6}$alkoxy, halogen, amino or aryl.

In the present context, the term "arylene" is intended to include divalent carbocyclic aromatic ring moieties, being either monocyclic, bicyclic or polycyclic, e.g. selected from the group consisting of phenylene and napthylene, optionally substituted with one or more $C_{1-6}$alkyl, $C_{1-6}$alkoxy, halogen, amino or aryl.

In the present context, the term "hetaryl" is intended to include monovalent heterocyclic aromatic ring moieties, being either monocyclic, bicyclic or polycyclic, e.g. selected from the group consisting of pyridyl, 1-H-tetrazol-5-yl, thiazolyl, imidazolyl, indolyl, pyrimidinyl, thiadiazolyl, pyrazolyl, oxazolyl, isoxazolyl, oxadiazolyl, thienyl, quinolinyl, pyrazinyl, or isothiazolyl, optionally substituted by one or more $C_{1-6}$alkyl, $C_{1-6}$alkoxy, halogen, amino or aryl.

In the present context, the term "hetarylene" is intended to include divalent heterocyclic aromatic ring moieties, being either monocyclic, bicyclic or polycyclic, e.g. selected from the group consisting of pyridinediyl, 1-H-tetrazolediyl, thiazoldiyl, imidazolediyl, indolediyl, pyrimidinediyl, thiadiazolediyl, pyrazolediyl, oxazolediyl, isoxazolediyl, oxadiazolediyl, thiophenediyl, quinolinediyl, pyrazinediyl, or isothiazolediyl, optionally substituted by one or more $C_{1-6}$alkyl, $C_{1-6}$alkoxy, halogen, amino or aryl.

In the present context, the term "heterocyclic system" is intended to include aromatic as well as non-aromatic ring moieties, which may be monocyclic, bicyclic or polycyclic, and contain in their ring structure at least one, such as one, two or three, nitrogen atom(s), and optionally one or more, such as one or two, other hetero atoms, e.g. sulphur or oxygen atoms. The heterocyclic system is preferably selected from pyrazole, pyridazine, triazine, indazole, phthalazine, cinnoline, pyrazolidine, pyrazoline, aziridine, dithiazine, pyrrol, imidazol, pyrazole, isoindole, indole, indazole, purine, pyrrolidine, pyrroline, imidazolidine, imidazoline, pyrazolidine, pyrazoline, piperidine, piperazine, indoline, isoindoline, or morpholine.

The term "halogen" is intended to include chlorine (Cl), fluorine (F), bromine (Br) and iodine (I).

EXEMPLIFICATION

The present invention will now be illustrated by the following Example, which are not intended to be limiting in any way.

Example 1

A double blind, placebo controlled, randomized study was designed to investigate the ability of growth hormone secretagogues to be used for the treatment of emetic conditions.

82 human subjects were enrolled in a 12 week parallel study. Of the 82 subjects, 74 subjects were classified in the intent to treat group (ITT). These 74 subjects all had active cancer, received at least one dose of study medication, and had at least one post-dose efficacy measurement. The 74 subjects were separated into two groups: the placebo group and the RC-1291 group. 30 of the 36 placebo group subjects and 33 of the 38 RC-1291 group subjects were receiving some form of chemotherapy. The RC-1291 group received 50 mg of RC-1291 in two 25 mg capsules daily. The placebo group received two capsules daily.

The effect of RC-1291 administered to cancer patients was compared to the effect of placebo administered to a similar group of patients. In order to determine the ability of RC-1291 to reduce a subject's cancer symptom burden, i.e. Quality-of-Life, subjects were administered the Anderson Symptom Assessment System (ASAS) test prior to, during and at the completion of the study. The ASAS test is conducted by asking subjects to rate on a 0-10 scale the severity of 10 symptoms: pain, fatigue, nausea, depression, anxiety, drowsiness, shortness of breath, appetite, sleep and feeling of well being (see, Palmer et al. (2005) *J. Pain and Symptom Management* 6:565-571). The text below reflects and inversion of the ASAS scores such that higher values reflect a better Quality-of-Life:

After the 12 week study during which patients received standard of care for nausea symptoms, patients administered RC-1291 reported an increase in total ASAS score relative to baseline of 1.52 versus a decrease in total ASAS score relative to baseline of 5.13 in patients administered placebo. The overall difference in total ASAS score between the two groups, 6.66, was statistically significant (p-0.0287), indicating a significantly increased Quality-of-Life and reduction in cancer symptom burden in RC-1291-treated patients versus patients receiving placebo. In particular, cancer patients treated with RC-1291 exhibited a statistically significant reduction in the ASAS nausea symptom scale relative to patients receiving placebo (overall difference between treatment groups=1.46, p=0.0046).

In a separate crossover study, 16 cancer patients were treated with RC-1291 or placebo as described above for 3 days, washed out for ~5 days and then administered placebo or RC-1291 (whichever one they had not received in the initial 3 day period). 12 of 16 placebo group subjects and 11 of the 16 RC-1291 group subjects were receiving some form of chemotherapy.

An overall difference in the ASAS nausea symptom scale was observed between the two treatments: Decreased nausea was observed with RC-1291 treatment and increased nausea was observed with placebo treatment. The overall difference between treatments, 0.71, approached statistical significance (p=0.0756). These results demonstrate that RC-1291 has a sudden onset of anti-nausea effects that occur within 3 days. Overall, these results demonstrate that, unlike the ghrelin peptide which has been shown to be anti-emetic only when administered intracerebroventricurarly, ghrelin receptor agonists such as RC-1291 exhibit anti-emetic properties when administered systemically, e.g., orally.

Example 2

A Pharmacological Study of the Assessment of the Anti-emetic Activity of Ipamorelin in the Ferret The purpose of this study was to evaluate the anti-emetic response of Ipamorelin following a single intravenous injection (slow bolus) in ferrets treated with cisplatin.

Methods and Experimental Design 30 male ferrets (24-weeks old) were used in this experiment. Subsequent to arrival, all animals were subjected to a general physical examination by a qualified member of the veterinary staff to ensure normal health status. An acclimation period of at least one week was allowed between the animal receipt and the start of treatment in order to accustom the animals to the laboratory environment.

Animals were housed individually in stainless steel cages with a bar type floor equipped with an automatic watering valve. Each cage was clearly labeled with a color-coded cage card indicating project, group, animal numbers and sex. Each animal was uniquely identified with an ear tag.

Animals were randomized into the following groups:

| Group/ Identification | Dose Level (mg/kg/ dose)[a,b] | Dose Concentration (mg/mL) | Dose Volume (mL/kg/dose)[b] | Male Numbers |
|---|---|---|---|---|
| 1/Saline Control | 0 | 0 | 5 | 101-103, 114[c], 105-107 |
| 2/Ghrelin | 0.25 | 0.05 | 5 | 201-205 |
| 3/Ipamorelin | 1.0 | 0.2 | 5 | 301-307 |

[a]Cisplatin (10 mg/kg) was administered as a single intraperitoneal injection prior to the control/reference/test article administration.
[b]Animals received two separate intravenous injections of control/reference/test article. The first was administered immediately following cisplatin administration; the second was administered 30 minutes later.
[c]Animal No. 104 was replaced by Animal No. 114 prior to treatment due to general health conditions.

Preparation of Dose Formulations

Prior to dosing, the appropriate amounts of test article were dissolved in the vehicle to prepare a 4 mg/mL stock solution, and two equivalents of glacial acetic acid were added when formulating the stock solution (4 mg/mL) and the pH adjusted to 7.5±0.2 (if required) by addition of 1 N NaOH. The stock solution was subsequently sterile filtered using 0.22 μm PVDF filters, aliquoted for each day of dosing and stored frozen (ca. −20° C.) pending use for the dose formulation preparation.

The test article dose formulations were prepared on each day of dosing. The appropriate aliquot of the 4 mg/mL stock solution of test article was thawed at room temperature. An appropriate amount of stock solution (4 mg/mL) was then diluted with an appropriate volume of vehicle (0.9% Sodium Chloride Injection) to achieve the desired final concentration.

The ghrelin formulations were prepared on each day of dosing. The required amount of reference article was mixed with the appropriate volume of vehicle (0.9% Sodium Chloride Injection) to achieve the desired final concentration.

The cisplatin formulations were prepared once for both days of dosing. The required amount of cisplatin was mixed with the appropriate volume of vehicle (0.9% Sodium Chloride Injection) to achieve the desired final concentration. The cisplatin formulations was stored refrigerated (2-8° C.), protected from light pending use.

Preparation of Test Animals
Administration

Ferrets were food deprived overnight prior to dosing for an approximate 16 hour period.

Approximately 15 minutes prior to the start of dosing, all animals received approximately 50 g (half a can) of commercially available feline food.

Dosing occurred on consecutive days with approximately equal numbers of animals from each group being dosed on each day. Immediately following a single intraperitoneal injection of cisplatin, the control/reference/test article was administered via a slow intravenous injection via the cephalic or saphenous vein. Thirty minutes later, a second slow intravenous injection of the control/reference/test article was administered via a slow intravenous injection via the cephalic or saphenous vein. On each occasion, the dose volume was 5 mL/kg (cisplatin as well as control/reference/test article) and the actual dose administered was based on the most recent practical body weight of each animal.

Anti-Emetic Response Assay

Following dosing, the ferrets were monitored and observed for episodes of emesis for an approximate four hour period, which was subdivided into 10-minute intervals. The time prior to the first episode of retching or vomiting was recorded (latent period), as well the total number of retching and vomiting periods, over each 10-minute interval, through the overall observation period (4 hours post dose).

For the purposes of this study, episodes of emesis were defined as rhythmic abdominal contractions associated with oral expulsion of solid or liquid material from the gastrointestinal tract (i.e. vomiting) or not associated with the passage of material (i.e. retching). An episode of retching and/or vomiting was considered separate when an animal changed position in the cage or when the interval between retches and/or vomits exceeds an approximate 5 second period.

Statistical Methods

Numerical data obtained from animals was subjected to calculation of group means and standard errors of the mean (SEM). The following statistical comparisons were performed.

The anti-emetic response was evaluated using the individual observation for: the latent period, the average of retching episodes per 10-minute interval with presence of retching, the average of vomiting episodes per 10-minute interval with presence of vomiting, the total frequency of retching episodes for the observation period, the total frequency of vomiting episodes for the observation period, the total number of 10-minute intervals with presence of retching and the total number of 10-minute intervals with presence of vomiting. Whenever there was no retching or vomiting episode for the whole animal observation period, the latent period was set to 4 hours and the average of retching/vomiting episodes per interval with presence of retching/vomiting was set to zero. Each of these seven parameters was submitted to the following statistical comparison.

The non-parametric Kruskal-Wallis test was used to compare all considered groups. If the Kruskal-Wallis test was significant (p<0.05), then the Saline Control group was compared to each treated group using Dunn's test.

Results

Mortality and Clinical Signs

There were no deaths and no clinical signs noted in this study related to dosing.

Anti-Emetic Response

Saline control animals exhibited an average of 4.89 and 1.78 retching and vomiting episodes during the 4-hour observation period, respectively.

Ghrelin treated animals exhibited an average of 7.00 and 1.60 retching and vomiting episodes during the 4-hour observation period, respectively. Neither the onset time nor the numbers of retches or vomits were statistically different from the saline control animals.

In contrast, ipamorelin-treated animals exhibited an average of 1.14 and 0.75 retching and vomiting episodes during the 4-hour observation period, respectively. Ipamorelin-treated animals exhibited a modest, non-statistically significant ($p>0.05$) delay in the onset time of emetic response following cisplatin administration. The 82% reduction in number of retching episodes compared to saline control animals reached statistical significance ($p<0.05$). The reduction in vomiting episodes relative to saline control animals failed to reach statistical significance ($p>0.05$).

CONCLUSION

In conclusion, ipamorelin administered intravenously to male ferrets at 1.0 mg/kg/dose significantly decreased the number of retching episodes when compared to saline-treated controls ($p \leq 0.05$). The effect of ipamorelin on decreasing number of vomiting episodes did not reach statistical significance versus the saline-treated control group animals.

Ghrelin administered intravenously at a dose of 0.25 mg/kg/dose (i.v.) did not display a significant efficacy relative to the control animals.

What is claimed is:

1. A method of treating emesis induced by cancer chemotherapy or post-operative nausea and vomiting in a subject comprising administering to a subject in need of such treatment, a treatment effective amount of a compound of structure III, or a pharmaceutically acceptable salt thereof:

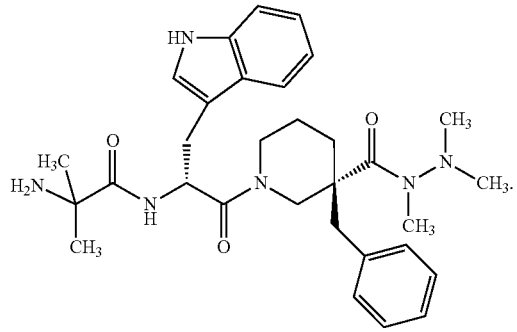

III

2. The method of claim 1, wherein said emesis is post-operative nausea and vomiting.

3. The method of claim 1, wherein said emesis is induced by cancer chemotherapy.

4. The method of claim 1, wherein the compound is administered at an amount of from 1 to 150 mg/day.

5. The method of claim 1, wherein the compound is administered at an amount of from 10 to 100 mg/day.

6. The method of claim 1, wherein the compound is administered at an amount of about 50 mg/day.

7. The method of claim 1 wherein the compound is administered in an amount of about: 200 mcg, 300 mcg, 400 mcg, 500 mcg, 1 mg, 1.25 mg, 1.5 mg, 2.0 mg, 2.5 mg, 3.0 mg, 3.5 mg, 4.0 mg, 4.5 mg, 5 mg, 10 mg, 20 mg, 30 mg, 40 mg, or 50 mg.

8. The method of claim 1, wherein the subject is receiving cancer chemotherapy.

9. The method of claim 1, wherein said treatment is defined by an increase in the period of latency of an emetic episode in a subject.

10. The method of claim 1, wherein said treatment is defined based on a reduction in the number of episodes of nausea and vomiting.

11. A method of increasing the period of latency in a subject prior to an episode of emesis wherein the episode of emesis is induced by cancer chemotherapy or wherein the episode of emesis is post-operative, comprising administering to a subject in need of such treatment, a treatment effective amount of a compound of structure III, or a pharmaceutically acceptable salt thereof:

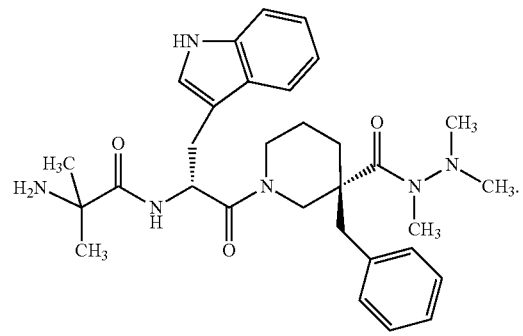

III

12. The method of claim 11, wherein the compound is administered in an amount of from 1 mg to 150 mg.

13. The method of claim 11, wherein the compound is administered in an amount of from 10 mg to 100 mg.

14. A method of reducing the number of episodes of retching in a subject induced by cancer chemotherapy or post-operative nausea and vomiting, comprising administering to a subject in need of such treatment, a treatment effective amount of a compound of structure III, or a pharmaceutically acceptable salt thereof:

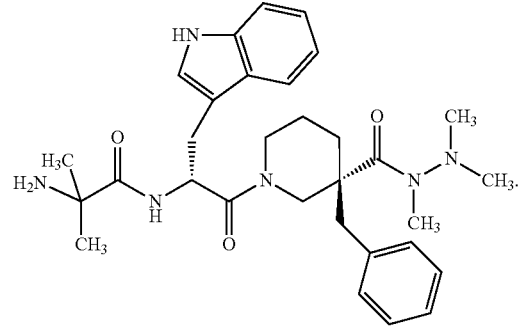

III

15. The method of claim 14, wherein the compound is administered in an amount of from 1 mg to 150 mg.

16. The method of claim 14, wherein the compound is administered in an amount of from 10 mg to 100 mg.

* * * * *